US008791080B2

(12) United States Patent
Fernandes

(10) Patent No.: US 8,791,080 B2
(45) Date of Patent: Jul. 29, 2014

(54) METHODS FOR TREATING GASTROINTESTINAL DISEASES

(75) Inventor: Prabhavathi B. Fernandes, Chapel Hill, NC (US)

(73) Assignee: Cempra Pharmaceuticals, Inc., Chapel Hill, NC (US)

( * ) Notice: Subject to any disclaimer, the term of this patent is extended or adjusted under 35 U.S.C. 154(b) by 140 days.

(21) Appl. No.: 13/125,551

(22) PCT Filed: Oct. 24, 2009

(86) PCT No.: PCT/US2009/061976
§ 371 (c)(1),
(2), (4) Date: Apr. 21, 2011

(87) PCT Pub. No.: WO2010/048599
PCT Pub. Date: Apr. 29, 2010

(65) Prior Publication Data
US 2011/0237534 A1   Sep. 29, 2011

Related U.S. Application Data

(60) Provisional application No. 61/108,134, filed on Oct. 24, 2008, provisional application No. 61/108,168, filed on Oct. 24, 2008, provisional application No. 61/108,110, filed on Oct. 24, 2008, provisional application No. 61/108,137, filed on Oct. 24, 2008, provisional application No. 61/108,112, filed on Oct. 24, 2008, provisional application No. 61/162,109, filed on Mar. 20, 2009.

(51) Int. Cl.
*A61K 31/70* (2006.01)
(52) U.S. Cl.
CPC ..................................... *A61K 31/70* (2013.01)
USPC .......................................................... 514/29
(58) Field of Classification Search
CPC .................................................. A61K 31/7048
USPC .......................................................... 514/29
See application file for complete search history.

(56) References Cited

U.S. PATENT DOCUMENTS

| | | | |
|---|---|---|---|
| 4,331,803 A | 5/1982 | Watanabe | |
| 4,474,768 A | 10/1984 | Bright | |
| 4,742,049 A | 5/1988 | Baker | |
| 5,444,051 A | 8/1995 | Agouridas | |
| 5,527,780 A | 6/1996 | Agouridas | |
| 5,543,400 A | 8/1996 | Agouridas | |
| 5,635,485 A | 6/1997 | Agouridas | |
| 5,656,607 A | 8/1997 | Agouridas | |
| 5,747,467 A | 5/1998 | Agouridas | |
| 5,760,233 A | 6/1998 | Agouridas | |
| 5,770,579 A | 6/1998 | Agouridas | |
| 5,834,428 A | 11/1998 | Drucker | |
| 5,985,844 A | 11/1999 | Heck | |
| 6,011,142 A | 1/2000 | Bonnet | |
| 6,020,521 A | 2/2000 | Randolph | |
| 6,028,181 A | 2/2000 | Or | |
| 6,096,714 A | 8/2000 | Agouridas | |
| 6,121,432 A | 9/2000 | Bonnet | |
| 6,395,710 B1 | 5/2002 | Chu | |
| 6,407,074 B1 | 6/2002 | Bronk | |
| 6,420,535 B1 | 7/2002 | Phan | |
| 6,437,106 B1 | 8/2002 | Stoner | |
| 6,440,941 B1 | 8/2002 | Denis | |
| 6,455,505 B2 | 9/2002 | Agouridas | |
| 6,515,116 B2 | 2/2003 | Suh | |
| 6,555,524 B2 | 4/2003 | Kaneko | |
| 6,664,238 B1 | 12/2003 | Su | |
| 6,777,393 B2 | 8/2004 | Bronk | |
| 6,809,188 B1 | 10/2004 | Suh | |
| 6,849,608 B2 | 2/2005 | Su | |
| 6,890,907 B2 | 5/2005 | Speirs | |
| 7,419,961 B2 | 9/2008 | Napoletano | |
| 7,601,695 B2 | 10/2009 | Liang | |
| 2002/0028781 A1 | 3/2002 | Agouridas | |
| 2003/0176327 A1 | 9/2003 | Cassell | |
| 2004/0009930 A1 | 1/2004 | Su | |
| 2005/0014706 A1 | 1/2005 | Falzari | |
| 2005/0022242 A1 | 1/2005 | Rosetti | |
| 2005/0153905 A1 | 7/2005 | Burger | |
| 2005/0222427 A1 | 10/2005 | Sharpless | |
| 2006/0100164 A1* | 5/2006 | Liang et al. ..................... 514/28 |
| 2006/0264385 A1 | 11/2006 | Wang | |
| 2007/0167382 A1 | 7/2007 | Finkelstein | |
| 2007/0197518 A1 | 8/2007 | Johnson et al. | |
| 2008/0113926 A1 | 5/2008 | Ivezic | |
| 2008/0221048 A1 | 9/2008 | Woo | |
| 2008/0287376 A1 | 11/2008 | Das | |
| 2009/0075916 A1 | 3/2009 | Upadhyay | |
| 2009/0156517 A1 | 6/2009 | Zhang | |

FOREIGN PATENT DOCUMENTS

| | | |
|---|---|---|
| EP | 0248279 A2 | 12/1987 |
| EP | 0680967 A1 | 11/1995 |
| EP | 1024145 A2 | 8/2000 |
| WO | 9830574 A1 | 7/1998 |
| WO | 9856800 A1 | 12/1998 |
| WO | 9921866 A1 | 5/1999 |
| WO | 9928311 A1 | 6/1999 |
| WO | 0012521 A1 | 3/2000 |
| WO | 0031099 A1 | 6/2000 |
| WO | 0044761 A2 | 8/2000 |

(Continued)

OTHER PUBLICATIONS

Zuckerman, "Macrolides and ketolides: azithromycin, clarithromycin, telithromycin", Infectious Disease Clinics of North America, vol. 18, (2004), pp. 621-649.*

Barcia-Macay, Maritza, et al., "Pharmacodynamic evaluation of the intracellular activities of antibodies against *Staphylococcus aureus* in a model of THP-1 macrophages," Mar. 2006, Antimicrobial Agents and Chemotherapy, vol. 50, No. 3, pp. 841-51.

(Continued)

*Primary Examiner* — Elli Peselev
(74) *Attorney, Agent, or Firm* — Barnes & Thornburg LLP

(57) ABSTRACT

Described herein are macrolide and ketolide antibiotics and pharmaceutical compositions, methods, and uses thereof for treating gastrointestinal diseases.

8 Claims, 7 Drawing Sheets

(56) References Cited

FOREIGN PATENT DOCUMENTS

| WO | 0062783 A2 | 10/2000 |
|---|---|---|
| WO | 0110878 A1 | 2/2001 |
| WO | 0250092 A1 | 6/2002 |
| WO | 03004509 | 1/2003 |
| WO | 03004509 A2 | 1/2003 |
| WO | 03072141 A1 | 9/2003 |
| WO | 2004080391 A2 | 9/2004 |
| WO | 2005105821 | 11/2005 |
| WO | 2007059307 A2 | 5/2007 |
| WO | 2009055557 | 4/2009 |

OTHER PUBLICATIONS

Crone, Julia, et al., "Evaluation of a monoclonal antibody-based test for detection of *Helicobacter pylori*-Specific Antigen in stool samples from mice," Jul. 2004, Clinical and Diagnostic Laboratory Immunology, vol. 11, No. 4, pp. 799, 800.
Laine, Loren, et al., "Prospective comparison of H&E, Giemsa and Genta stains for the diagnosis of *Helicobacter pylori*," 1997, Gastrointestinal Endoscopy, vol. 45, No. 6, pp. 463-467.
Lee, Adrian, et al., "A standard mouse model of *Helicobacter pylori* infection: introducing the Sydney Strain," 1997, Gastroenterology, vol. 112, pp. 1386-1397.
Liang, Chang-Hsing, et al. "Synthesis and biological activity of new 5-O-sugar modified ketolide and 2-fluoro-ketolide antibiotics." *Bioorganic & medicinal chemistry letters* 15.5 (2005): 1307-1310.
LeMahieu, R. A., Carson, M., and Kierstead, R. W., 'Glycoside Cleavage Reactions on erythromycin A. Preparation of Erythronolide A,' Journal of Medicinal Chemistry, vol. 17, Vo. 9, 1974, 953-956.
Romero et al., 'An efficient entry to new sugar modified ketolide antibiotics' Tetrahedron Letters, vol. 46, 2005, pp. 1483-1487.
Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.
Vince, R., Almquist, R. G., Ritter, C. L., and Daluge, S., Antimicrobial Agents and Chemotherapy, vol. 8, No. 4, 1975, 439-443.
Or et al., 'Design, Synthesis, and Antimicrobial Activity of 6-O-Substituted Ketolides Active Against Resistant Respiratory Tract Pathogens', J. Med. Chem., 43:1045-49 (2000).
Champney et al., 'Structure-Activity Relationships for Six Ketolide Antibiotics', Current Microbiology, 42:203-10 (2001).
Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).
Torne et al. 'Peptidotriazoles on Solid Phase: [1,2,3]-Triazoles by Regiospecific Copper(I)-Catalyzed 1,3-Dipolar Cycloadditions of Terminal Alkynes to Azides', J. Org. Chem., 67:3057-64 (2002).
Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).
Baker, W.R. et al., 'Modification of macrolide antibiotics. Synthesis of 11-deoxy-11-(carboxyamino)-6-0-methylerythromycin A 11,12-(cyclic esters) via an intramolecular Michael reaction of O-carbamates with an alpha , beta -unsaturated ketone,' J. Org. Chem., 53:2340-2345, 1988.
Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).
Phan, L.T. et al., 'Synthesis of 2-Fluoro-6-0-propargyl-11,12-carbamate Ketolides. A Novel Class of Antibiotics,' Org. Ltrs., 2:2951-2954 (2000).
Plata et al., "The synthesis of ketolide antibiotic ABT-773 (cethromycin)," Tetrahedron, vol. 60, 2004, pp. 10171-10180.
Holzer, G., et al., "Ka1,2 and KB1,3 X-Ray Emission Lines of the 3d Transition Metals", Dec. 1997, Physical Review, vol. 56, No. 6, pp. 4554-4568.
Berge, Stephen M., et al., "Pharmaceutical Salts", 1977, Journal of Pharmaceutical Sciences, vol. 66, No. 1, pp. 1-19.

Bermudez, Luiz E., et al., "Telithromycin is Active Against Mycobacterium Avium in Mice Despite Lacking Significant Activity in Standard in Vitro and Macrophage Assays and Is Associated with Low Frequency of Resistance During Treatment", 2001, Antimicrobal Agents and Chemotherapy, vol. 45, No. 8, pp. 2210-2214.
Bermudez, Luiz E., et al., "EDP-420, a Bicyclolide (Bridged Bicyclic Macrolide), Is Active Against Mcyobacterium Avium", 2007, Antimicrobal Agents and Chemotherapy, vol. 51, No. 5, pp. 1666-1670.
Cynamon, M. H., et al., "Activity of ABT-773 Against Mycobacterium Avium Complex in the Beige Mouse Model", 2000, Antimicrobal Agents and Chemotherapy, vol. 44, No. 10, pp. 2895-2896.
Patel, Ramesh N., "Stereoselective Biocatalysis", 2000, Bristol-Myers Squibb Research Institute; pp. 775-797.
Vennerstrom, Jonathan L., et al., "Identification of an Antimalarial Synthetic Trioxolane Drug Development Candidate", 2004, Letters to Nature, vol. 430, pp. 900-904.
Bebear, C.M., et al., In vitro activity of trovafloxacin compared to those of five antimicrobials against mycoplasmas including *Mycoplasma hominis* and *Ureaplasma urealyticum* fluoroquinolone-resistant isolates that have been genetically characterized, Antimicrob Agents Chemother 44:2557-2560 (2000).
Duffy, L., et al., Fluoroquinolone resistance in *Ureaplasma parvum* in the United States, J Clin Microbiol 44:1590-1591 (2006).
Waites, K.B., et al., Mycoplasmas and ureaplasmas as neonatal pathogens, Clin Microbiol Rev 18:757-89 (2005).
Drusano, G. L., et al., "Is 60 Days of Ciprofloxacin Adminstration Necessary for Postexposure Prophylaxis for *Bacillus anthracis*?", 2008, Antimicrobial Agents and Chemotherapy. vol. 52, No. 11, pp. 3973-3979.
Feder, P. I., et al., 1991. Statistical Analysis of Dose-Response Experiments by Maximum Likelihood analysis and Iteratively Reweighted Nonlinear Least Squares Regression Techniques, 1991, Drug Information Journal, vol. 28, pp. 323-334.
Inglesby, Thomas V., et al., "Anthrax as a Biological Weapon, 2002", 2002, Journal of the American Medical Association, vol. 287, No. 17, pp. 2236-2252.
Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.
Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Physicians' Desk Reference, p. 2905, (2007).
Nilius et al.: 'Ketolides: the future of the macrolides?' Current Opinion in Pharmacology, [Online] vol. 2, Jan. 14, 2002, pp. 1-8 Retrieved from the Internet: <URL:http://www.sciencedirect.com/science/article/pii/S1471489202001984>.
Jensen, J.S., et al., Azithromycin Treatment Failure in *Mycoplasma genitalium*Positive Patients with Nongonococcal Urethritis Is Associated with Induced Macrolide Resistance, Clin Infect Dis 47:1546-53 (2008).
Li, X., et al., Emerging macrolide resistance in *Mycoplasma pneumoniae* in children: detection and characterization of resistant isolates, Pediatr Infect Dis J, 28:693-696 (2009).
Lemair, Sandrine, et al. "Cellular Accumulation and Pharmacodynamic Evaluation of the Intracellular Activity of CEM-101, a Novel Fluoroketolide, Against *Staphylococcus aureus, Listeria monocytogenes* and *Legionella neumophila* in Human THP-1 Macrophages", 2009, Antimicrobial Agents and Chemotherapy. vol. 53, No. 9, pp. 3734-3743.
European Search Report for EP 09 82 2827, dated Mar. 21, 2012.
Caira MR, "Crystalline polymorphism of orgainic compounds," Design of Organic Solids, Topics in Current Chemistry, Springer Berlin Heidelberg, 1998, p. 163-208.
Pathak et al., "Enzymatic Protecting Group Techniques in Organic Synthesis," Stereosel, Biocatal., 2000; pp. 775-797.

* cited by examiner

METHODS FOR TREATING GASTROINTESTINAL DISEASES

CROSS-REFERENCE TO RELATED APPLICATIONS

This application is a U.S. national application under 37 C.F.R. §371 (b) of International Application Ser. No. PCT/US2009/061976 filed Oct. 24, 2009, which claims priority under 35 USC §119(e) to U.S. Provisional Application Ser. No. 61/108,110, filed on Oct. 24, 2008, U.S. Provisional Application Ser. No. 61/108,112, filed on Oct. 24, 2008, U.S. Provisional Application Ser. No. 61/108,134, filed on Oct. 24, 2008, U.S. Provisional Application Ser. No. 61/108,137, filed on Oct. 24, 2008, U.S. Provisional Application Ser. No. 61/108,168, filed on Oct. 24, 2008, U.S. Provisional Application Ser. No. 61/162,109, filed on Oct. 24, 2008, U.S. Provisional Application Ser. No. incorporated herein by reference.

TECHNICAL FIELD

The invention described herein relates to the treatment of gastrointestinal diseases. In particular, the invention described herein relates to the treatment of gastrointestinal diseases with macrolide and ketolide antibiotics.

BACKGROUND AND SUMMARY OF THE INVENTION

Most of the bacteria in the small intestine are Gram-positive, while those in the colon are mostly Gram-negative. The first part of the colon is mostly responsible for fermenting carbohydrates, while the latter part mostly breaks down proteins and amino acids. Bacterial growth is rapid in the cecum and ascending colon, which has a low pH, and correspondingly slow in the descending colon, which has an almost neutral pH. The body maintains the proper balance and locations of species by altering pH, the activity of the immune system, and peristalsis.

Gastritis is an inflammation of the lining of the stomach. There are many possible causes. Gastritis may be caused by excessive alcohol consumption, or the prolonged use of non-steroidal anti-inflammatory drugs, also known as NSAIDs, such as aspirin or ibuprofen. Sometimes gastritis develops after major surgery, traumatic injury, burns, or severe infections. Certain diseases, such as pernicious anemia and chronic bile reflux, or autoimmune disorders, can cause gastritis as well. Importantly, gastritis may be caused by infection with bacteria, such as *Helicobacter pylori*. The most common symptom is abdominal upset or pain. Other symptoms are indigestion, abdominal bloating, nausea, and vomiting, or a feeling of fullness or burning in the upper abdomen.

Gastroenteritis is inflammation of the gastrointestinal tract, involving both the stomach and the small intestine, often resulting in acute diarrhea. The inflammation is caused most often by infection with certain viruses, but may also be caused by bacteria or parasites. Worldwide, inadequate treatment of gastroenteritis kills 5 to 8 million people per year, and is a leading cause of death among infants and children under 5. Similarly, enteritis refers to inflammation of the small intestine with similar causes.

Many different bacteria can cause gastroenteritis, including *Salmonella, Shigella, Staphylococcus, Campylobacter jejuni, Clostridium, Escherichia coli, Yersinia*, and others. Some sources of the infection are improperly prepared food, reheated meat dishes, seafood, dairy, and bakery products. Each organism causes slightly different symptoms but all result in diarrhea. Colitis, inflammation of the large intestine, may also be present.

Several *Salmonella* species are capable of causing gastroenteritis, including *S. enterica*, which is subdivided into several serovars. Illustrative examples include Serovar Typhi (previously known as *S. Typhi*), which is the disease agent responsible for typhoid fever, and Serovar Typhimurium (also known as *S. Typhimurium*), which leads to a form of human gastroenteritis sometimes referred to as salmonellosis. Several *Shigella* species are also responsible for gastroenteritis. Illustrative examples include *S. boydii; S. dysenteriae*, which is a major cause of dysentery; *S. flexneri*; and *S. sonnei*. An illustrative species of *Campylobacter* causing gastroenteritis in humans is *C. jejuni*. It is one of the most common causes of human gastroenteritis in the world. *Yersinia* species are also a cause of gastroenteritis, an illustrative example is the zoonotic *Y. enterocolitica*. The disease caused by *Y. enterocolitica* is called yersiniosis. Some strains of *Helicobacter* are pathogenic to humans and are strongly associated with peptic ulcers, chronic gastritis, duodenitis, and stomach cancer. An illustrative species responsible for disease in humans is *H. pylori*.

Reportedly clarithromycin (CLR) is the only known macrolide antibiotic that works in vivo on *Helicobacter pylori*. Although other macrolide antibiotics show in vitro activity against *H. pylori*, there often are not sufficiently active at low pH to work in vivo. In addition, may antibiotics, such as azithromycin (AZI) and telithromycin (TEL), do not achieve sufficiently high tissue and blood circulating levels to show efficacy on *H. pylori*. Without being bound by theory, it is suggested herein that high protein binding may prevent other macrolide antibiotics from having such in vivo activity. Ordinarily, a minimum pH is required for macrolide antibiotics to show activity.

It has been surprisingly discovered herein that triazole-containing macrolides, including ketolides, exhibit high antibacterial activity at low pH, or at pH levels much lower than the minimum pH required by other macrolide antibiotics for efficacy. It has also been unexpectedly discovered herein that the compounds described herein have high anti-bacterial activity against gastroenteritis disease pathogens (GDP), such as *H. pylori* (HP), and gastritis and diarrhea illness pathogens, such as *Campylobacter jejuni* (CJ), *Salmonella* spp. (SAL) and *Shigella* spp. (SHI).

In one illustrative embodiment, compounds of Formula (I) are described herein

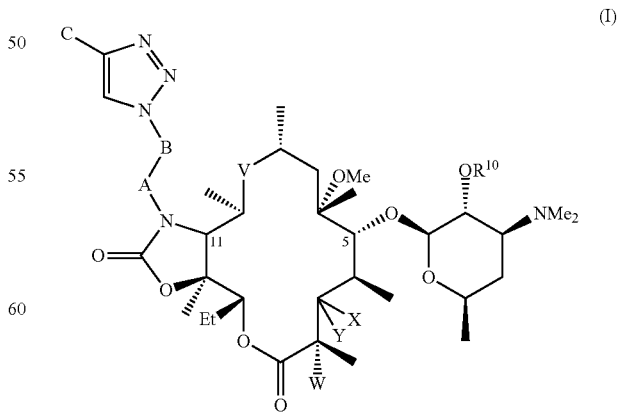

including pharmaceutically acceptable salts, hydrates, solvates, esters, and prodrugs thereof.

In one aspect, $R_{10}$ is hydrogen or acyl. In another aspect, X is H; and Y is $OR_7$; where $R_7$ is a monosaccharide or disaccharide, alkyl, aryl, heteroaryl, acyl, or $C(O)NR_8R_9$, where $R_8$ and $R_9$ are each independently selected from the group consisting of hydrogen, hydroxy, alkyl, arylalkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl.

In another aspect, V is C(O), C(=$NR_{11}$), CH($NR_{12}$, $R_{13}$), or N($R_{14}$)$CH_2$, where N($R_{14}$) is attached to the C-10 carbon of the compounds of Formulae 1 and 2; wherein $R_{11}$ is hydroxy or alkoxy, $R_{12}$ and $R_{13}$ are each independently selected from the group consisting of hydrogen, hydroxy, alkyl, arylalkyl, alkylaryl, alkoxy, heteroalkyl, aryl, heteroaryl, dimethylaminoalkyl, acyl, sulfonyl, ureido, and carbamoyl; $R_{14}$ is hydrogen, hydroxy, alkyl, aralkyl, alkylaryl, alkoxy, heteroalkyl, aryl, heteroaryl, dimethylaminoalkyl, acyl, sulfonyl, ureido, or carbamoyl.

In another aspect, W is H, F, Cl, Br, I, or OH.

In another aspect, A is $CH_2$, C(O), C(O)O, C(O)NH, $S(O)_2$, $S(O)_2NH$, C(O)NHS(O)$_2$. In another aspect, B is $(CH_2)_n$ where n is an integer ranging from 0-10, or B is an unsaturated carbon chain of 2-10 carbons. In another aspect, C is hydrogen, hydroxy, alkyl, aralkyl, alkylaryl, alkoxy, heteroalkyl, aryl, heteroaryl, aminoaryl, alkylaminoaryl, acyl, acyloxy, sulfonyl, ureido, or carbamoyl.

In another embodiment, compositions including a therapeutically effective amount of one or more compounds of formula (I), or the various subgenera thereof are described herein. The pharmaceutical compositions may include additional pharmaceutically acceptable carriers, diluents, and/or excipients.

In another embodiment, methods are described herein for treating diseases arising from pathogenic organism populations causing enteritis, gastroenteritis, and/or a related disease. The methods include the step of administering a therapeutically effective amount of one or more compounds of formula (I), or the various subgenera thereof are described herein, to a patient in need of relief or suffering from a disease caused by a pathogenic organism.

In another embodiment, uses are described herein for the manufacture of medicaments. The medicaments include a therapeutically effective amount of one or more compounds of formula (I), or the various subgenera thereof are described herein, or one or more compositions thereof described herein. The medicaments are suitable for treating diseases, such as enteritis, gastroenteritis, and/or a related disease arising from pathogenic organism populations.

In another embodiment, compounds, compositions, methods, and medicaments are described herein for treating diseases caused by *H. pylori*.

Each embodiment of the compositions, methods, and medicaments include a therapeutically effective amount of one or more triazole-containing macrolides or ketolides, such as one or more compounds or formula (I). The therapeutically effective amount is administered to a patient in need of relief or suffering from the disease.

In another embodiment, compounds, compositions, methods, and medicaments are described herein for treating diseases caused by *H. pylori*. that include the co-administration of one or more proton pump inhibitors, such as but not limited to omeprazole, esopremazole, and the like.

In another embodiment, oral formulations of the compounds and compositions described herein include enteric coating. Without being bound by theory, it is believed herein that enteric coating may prevent stomach acid degradation of proton pump inhibitors to achiral intermediates.

In another embodiment, compounds, compositions, methods, and medicaments are described herein for treating enteritis, gastroenteritis, and related diseases, that include the co-administration of other antibiotics, including but not limited to fluoroquinolone antibiotics, metronidazoles, vancomycin, and the like, and combinations thereof.

In another embodiment, compounds, compositions, methods, and medicaments are described herein for treating enteritis, gastroenteritis, and related diseases, accompanied by diarrhea symptoms, that include the co-administration of other compounds for decreasing gut motility. It is appreciated that the macrolide compounds described herein may also decrease gut motility. Illustrative gut motility decreasing agents include but are not limited to loperamide, an opioid analogue commonly used for symptomatic treatment of diarrhea, and bismuth subsalicylate (BSS), an insoluble complex of trivalent bismuth and salicylate.

DETAILED DESCRIPTION

Figure 1:
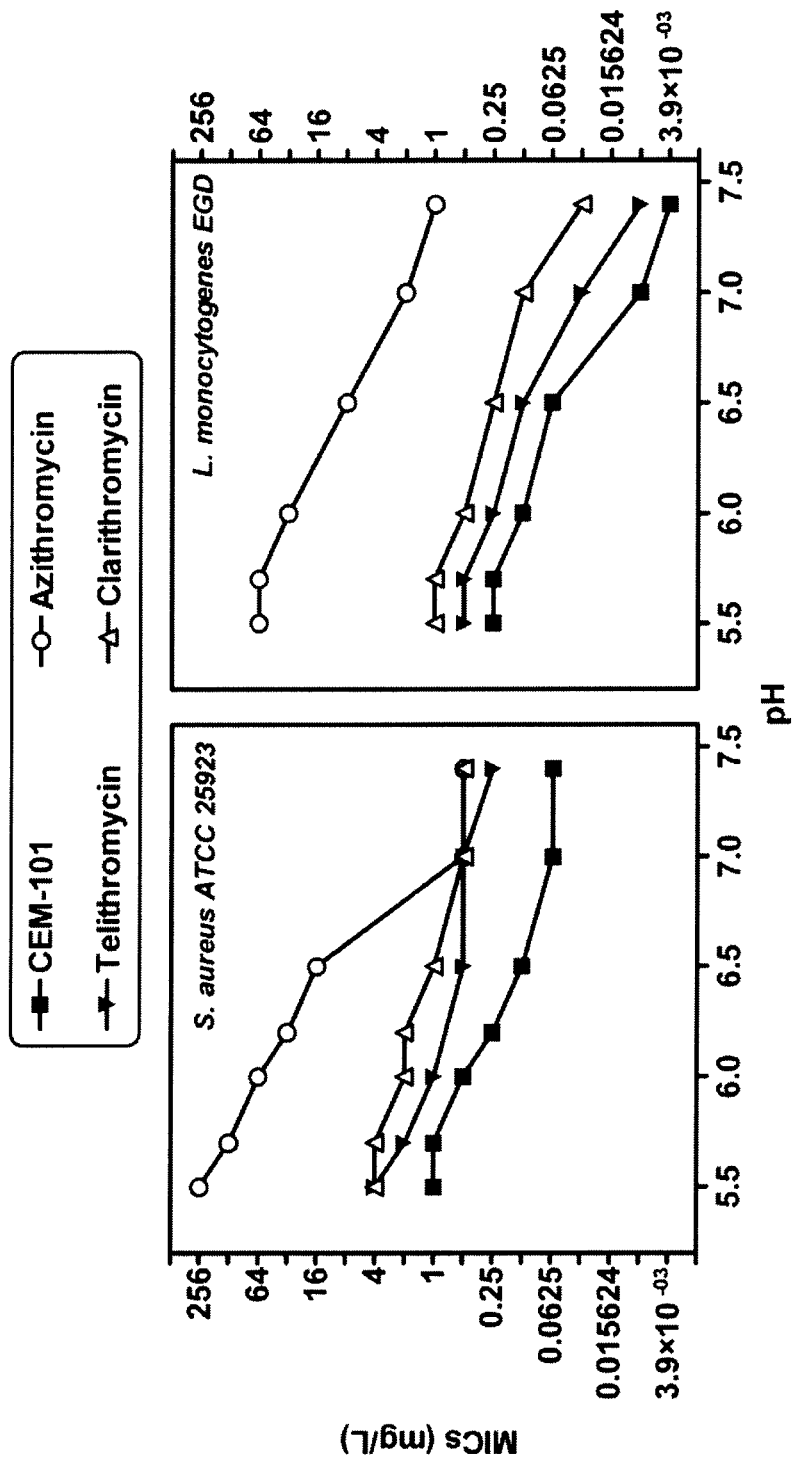
FIG. 1. Comparative susceptibilities of *S. aureus* ATCC 25923 and *L. monocytogenes* EGD to CEM-101, TEL, AZI, and CLR, based on MIC determinations in pH-adjusted broth.

In one embodiment, compositions, methods, and medicaments are described herein for treating diseases that are caused at least in part by GDP strains, where the compositions, methods, and medicaments include a therapeutically effective amount of a triazole-containing macrolide or ketolide compound described herein. In another embodiment, compositions, methods, and medicaments are described herein for treating CLR-resistant (CLR-R) gastric diseases, where the compositions, methods, and medicaments include a therapeutically effective amount of a triazole-containing macrolide or ketolide compound described herein.

In another embodiment, compounds are described herein that are active intracellularly. It has also been discovered herein that the intracellular accumulation and intracellular activity of triazole-containing macrolides was not affected by Pgp or Multidrug Resistant Protein (MRP) inhibitors. Accordingly, it is believed that the compounds described herein are not substrates or are poor substrates of P-glycoprotein (plasma or permeability gycoprotein, Pgp). It is appreciated that Pgp is an efflux mechanism that may lead to resistance by some organisms against certain antibiotics, such as has been reported for AZI and ERY in macrophages in which both antibiotics are substrates of the P-glycoprotein. Accordingly, it has been surprisingly found that the compounds described herein accumulate intracellularly. In addition to the intracellular accumulation, it has been surprisingly discovered that the triazole-containing macrolide and ketolide compounds described herein have high intracellular activity. It has also been surprising found herein that the compounds described herein have lower protein binding than is typical for macrolides at lower pH, such as the pH found in bacterial infections, including but not limited to abscesses. It is appreciated that the lack of intracellular activity typically observed with anti-bacterial agents, including other macrolides and ketolides, may be due to high protein binding, and/or to the relatively lower pH of the intracellular compartments, such as is present in abscesses.

However, even when not removed by active efflux, the concentration of other anti-bacterial agents, including other macrolides and ketolides, in macrophages may not be efficacious in treating disease because of the low pH of the lysozomal compartment. For example, the acidic environment prevailing in the phagolysosomes (where *S. aureus* sojourns during its intracellular stage) may impair the activity of antibiotics, such as the AZI, CLR and TEL. It has been unexpectedly found that the compounds described herein retain their anti-bacterial activity at low pH. It is appreciated that the intracellular activity of the compounds described herein may be an important determinant for fast and complete eradication and, probably also, for prevention of resistance in the target organism.

Lack of effective antimicrobial therapy results in intracellular survival of bacteria, which remains a major cause of bacterial spreading, life-threatening therapeutic failures, and establishment of chronic, relapsing infections. These situations are observed during the course of infections caused by many organisms causing gastrointestinal diseases, including *H. pylori, C. jejuni, Salmonella,* and *Shigella*.

While it has been reported that intracellular accumulation of an antibiotic is indicative of efficient activity against bacteria, pharmacodynamic evaluation of a large series of commonly used antibiotics has revealed that other parameters such as intracellular bioavailability and modulation of activity in the infected compartment are also important. The observations described herein confirm and extend previous observations made with macrolides in this context due to the surprising differential behavior exhibited by the triazole-containing macrolides described herein, compared to known macrolide and ketolides, such as TEL, AZI, and CLR.

It is surprisingly found that triazole-containing macrolides accumulate to a considerably larger extent than the comparators, including AZI, and consistently expresses greater potency (decreased values of $E_{50}$ and $C_s$) while showing similar maximal efficacy ($E_{max}$) to comparators. Without being bound by theory, it is believed that this indicates that the improvements resulting from the structural modifications introduced in CEM-101 relate to modulation of pharmacokinetic properties and intrinsic activity (including its reduced susceptibility to physico-chemical conditions prevailing in the infected compartment) rather than to a change in its mode of action. Thus, triazole-containing macrolides exhibit the essentially bacteriostatic character of macrolides, but express it better in the intracellular milieu and at considerably lower extracellular concentrations than the comparators.

Without being bound by theory, it is believed that the cellular accumulation of triazole-containing macrolides, such as CEM-101, results from the general mechanism of proton trapping of weak organic bases envisaged for all macrolides as accumulation is almost completely suppressed, in parallel with AZI, by exposure to acid pH or to the proton ionophore monensin. Based on the general model of diffusion/segregation of weak bases in acidic membrane-bound compartments, accumulation is determined by the number of ionizable groups and the ratios between the membrane permeability coefficients of the unionized and ionized forms of the drug. While CEM-101 has two ionizable functions, the pKa of the aminophenyltriazole is calculated to be less than 4, suggesting that the molecule is largely monocationic (similar to CLR and TEL) at neutral and even at lysosomal pH (~5). In contrast, AZI has two ionizable functions with $pK_a$s>6 and is therefore dicationic intracellularly. CEM-101, however, possesses a fluoro substituent in position 2, which should make it more lipophilic than CLR or TEL. Without being bound by theory, it is believed that the ratio of the permeability constants of the unionized and ionized forms of CEM-101 in comparison with LR or TEL may be as important as the number of ionizable functions to determine the level of cellular accumulation of weak organic bases. Without being bound by theory, it is believed that the greater cellular accumulation of CEM-101 may be partially due to its lack of susceptibility to Pgp-mediated efflux (which is expressed by THP-1 macrophages under our culture conditions) in contrast to AZI.

It has been observed that many known macrolides have a large volume of distribution, which it is believed is related to their ability to accumulate inside eukaryotic cells by diffusion/segregation in acidic compartments, namely lysosomes and related vacuoles. As a consequence, known macrolides had been considered candidates for the treatment of infections localized in these compartments. Thus, it might be assumed that macrolides are suitable for treating infections caused by typical intracellular pathogens. However, direct quantitative comparisons between intracellular and extracellular activities using facultative intracellular pathogens, such as *S. aureus* or *L. monocytogenes*, suggest that known macrolides express only a minimal fraction of their antibacterial potential intracellularly, especially considering their great intracellular accumulation. This minimized antibacterial potential against organisms replicating in phagolysosomes and related vacuoles is believed to be related to acidic pH which is known to reduce the activity of known macrolides. Another factor is that some organisms, such as *H. pylori, C. jejuni, Salmonella*, and *Shigella*, may actually replicate in other subcellular compartments. In addition, certain macrolides, such as AZI, are subject to active efflux from macrophages, which further contributes to suboptimal intracellular activity.

In contrast, the cellular accumulation and intracellular activity of the triazole-containing compounds described herein, using models that have been developed for the study of the intracellular pharmacodynamics of antibiotics, is substantially improved over known macrolides, including ketolides. Thus, the compounds described herein maintain the maximal efficacy of their MICs, and show greater potency against intracellular forms of for example, against gastrointestinal disease causing organisms, including *H. pylori, C. jejuni, Salmonella*, and *Shigella* compared to TEL, AZI, and CLR. Without being bound by theory, it is believed that this improved intracellular potency of the triazole-containing compounds described herein results from the combination of the higher intrinsic activity against gastrointestinal disease causing organisms, including *H. pylori, C. jejuni, Salmonella*, and *Shigella* coupled with the retained activity at low pH, and the ability to distribute to a wide variety of intracellular compartments.

In another embodiment, the triazole-containing macrolide and ketolide compounds have intracellular activity, such as intracellular activity against gastrointestinal disease causing organisms, including *H. pylori, C. jejuni, Salmonella*, and *Shigella*. It is appreciated that routine susceptibility testing are usually determined against extracellular bacterial only, and therefore may be misleading in their prediction of efficacy against intracellular organisms. In another embodiment, compounds, compositions, methods, and uses are described herein for treating a disease caused at least in part by an intracellular *H. pylori, C. jejuni, Salmonella*, and/or *Shigella*. In another embodiment, the disease caused by the *Staphylococcus* infection is a gastrointestinal disease. It is further appreciated that *H. pylori, C. jejuni, Salmonella*, and/or *Shigella* may include virulent strains, and thus treatment with bacteriostatic agents may be ineffective. For example, recurrence may be a problem when treating such strains. It has been unexpectedly discovered herein that the compounds described herein are also bactericidal and therefore useful in treating diseases caused by such strains of. *pylori, C. jejuni, Salmonella*, and/or *Shigella*.

In another embodiment, the compounds, methods, and medicaments described herein include a therapeutically effective amount of one or more compounds described herein, wherein the therapeutically effective amount is an amount effective to exhibit intracellular antibacterial activity.

In another embodiment, compounds are described herein that are bactericidal. In another embodiment, the compounds, methods, and medicaments described herein include a therapeutically effective amount of one or more compounds described herein, wherein the therapeutically effective amount is an amount effective to exhibit bactericidal activity, including in vivo bactericidal activity. It has been reported that macrolides are generally bacteriostatic. Bacteriostatic compounds do not kill the bacteria, but instead for example inhibit growth and reproduction of bacteria without killing them; killing is accomplished by bactericidal agents. It is understood that bacteriostatic agents must work with the immune system to remove the microorganisms from the body. Bacteriostatic antibiotics may limit the growth of bacteria via a number of mechanisms, such as by interfering with bacterial protein production, DNA replication, or other aspects of bacterial cellular metabolism. In contrast, bactericidal antibiotics kill bacteria; bacteriostatic antibiotics only slow their growth or reproduction. Penicillin is a bactericide, as are cephalosporins, all belonging to the group of β-lactam antibiotics. They act in a bactericidal manner by disrupting cell wall precursor leading to lysis. In addition, aminoglycosidic antibiotics are usually considered bactericidal, although they may be bacteriostatic with some organisms. They act by binding irreversibly to 30 s ribosomal subunit, reducing translation fidelity leading to inaccurate protein synthesis. In addition, they inhibit protein synthesis due to premature separation of the complex between mRNA and ribosomal proteins. The final result is bacterial cell death. Other bactericidal antibiotics include the fluoroquinolones, nitrofurans, vancomycin, monobactams, co-trimoxazole, and metronidazole.

In another embodiment, the compounds, compositions, methods, and medicaments described herein include a therapeutically effective amount of one or more compounds described herein, wherein the therapeutically effective amount is an amount effective to exhibit bactericidal activity against one or more gastrointestinal disease causing organisms, including *H. pylori, C. jejuni, Salmonella*, and *Shigella*. Without being bound by theory, it is believed herein that treating such diseases using bacteriostatic agents may be unsuccessful in two respects. First, simply stopping the progression of the disease with a bacteriostatic agent may be insufficient because the immune system may not intervene to assist in curing the disease at a necessary level. For example, some bacterial organisms are not killed by the immune system because they reside in intracellular compartments. Thus, once the treatment course has ended, rapid recurrence of disease may result. Second, because some portion of the bacterial population will likely be eliminated, the remaining population may be selected for resistance development. It is believed herein that an intracellularly active agent, and/or an intracellularly active and bactericidal agent, will be efficacious in treating such diseases. In one illustrative embodiment, compounds described herein that achieve an intracellular concentration of 20× the MIC of the targeted bacteria. It has been reported that most, if not all, macrolide antibiotics, though bactericidal in vitro, are only bacteriostatic in vivo. For example, as described hereinbelow, when the time between the last dose of compound was extended, the bioload reduction levels remained the same for the triazole-containing compounds described herein, indicating a bactericidal response. In contrast, the TEL and CLR dose groups demonstrated bioload increases when the time interval was extended. Thus, those latter two macrolide/ketolide agents demonstrated a more classical bacteriostatic response.

In another illustrative embodiment, compounds of Formula (I) are described herein where X and Y are taken together with the attached carbon to form a C(O) group. In another embodiment, X is H, Y is OR$^7$, where R$^7$ is a monosaccharide radical, such as cladinosyl. In another embodiment, compounds of Formula (I) are described herein where W is fluoro. In another embodiment, compounds of Formula (I) are described herein where A and B are taken together to form an alkylene group, including but not limited to propylene, butylene, and pentylene. In another embodiment, compounds of Formula (I) are described herein where A and B are taken together to form butylene. In another embodiment, compounds of Formula (I) are described herein where A and B are taken together to form pentylene. In another embodiment, compounds of Formula (I) are described herein where A and B are taken together to form butylenes and C is 2-pyridinyl or aminophenyl, such as 3-aminophenyl. In another embodiment, compounds of Formula (I) are described herein where A and B are taken together to form propylenes, butylenes, or pentylenes; and C is aminophenyl, such as 3-aminophenyl. In another embodiment, compounds of Formula (I) are described herein where A and B are taken together to form pentylene and C is 3-pyridinyl or benzotriazole. In another embodiment, compounds of Formula (I) are described herein where C is an optionally substituted aryl or heteroaryl group. In another embodiment, compounds of Formula (I) are described herein where V is a carbonyl group. In another embodiment, compounds of Formula (I) are described herein where R$^{10}$ is hydrogen. In another embodiment, X is H, Y is OR$^7$, where R$^7$ is a monosaccharide radical, such as cladinosyl, and C is 3-pyridinyl or benzotriazolyl.

In another embodiment, C is optionally substituted phenyl, such as phenyl, halophenyl, haloalkylphenyl, aminophenyl, and the like, optionally substituted pyridinyl, such as 2-pyridinyl and 3-pyridinyl, optionally substituted benzotriazole, and the like.

In another embodiment, A and B are taken together to form butylene or pentylene, and X and Y are taken together with the attached carbon to form a C(O) group.

In another embodiment, compounds described in any of the preceding embodiments wherein V is C(O) are described. In another embodiment, compounds described in any of the preceding embodiments wherein W is H or F are described. In another embodiment, compounds described in any of the preceding embodiments wherein A is CH$_2$, B is (CH$_2$)$_n$, and n is an integer from 2-4 are described. In another embodiment, compounds described in any of the preceding embodiments wherein C is aryl or heteroaryl are described. In another embodiment, compounds described in any of the preceding embodiments wherein C is 3-aminophenyl or 3-pyridinyl are described. In another embodiment, compounds described in any of the preceding embodiments wherein R$_{10}$ is hydrogen. In another embodiment, compounds described in any of the preceding embodiments wherein A and B are taken together to form butylene or pentylene, and X and Y are taken together with the attached carbon to form a C(O) group. In another embodiment, compounds described in any of the preceding embodiments wherein A and B are taken together to form butylene or pentylene, and X and Y are taken together with the attached carbon to form a C(O) group, and W is F.

In another embodiment, an antibacterial composition is described herein, wherein the composition includes an effective amount of one or more compounds described herein, and a pharmaceutically acceptable carrier, excipient, or diluent therefor, or a combination thereof.

As used herein, the term "composition" generally refers to any product comprising the specified ingredients in the specified amounts, as well as any product which results, directly or indirectly, from combinations of the specified ingredients in the specified amounts. Illustratively, compositions may include one or more carriers, diluents, and/or excipients. The compounds described herein may be formulated in a therapeutically effective amount in conventional dosage forms for the methods described herein, including one or more carriers, diluents, and/or excipients therefor. Such formulation compositions may be administered by a wide variety of conventional routes for the methods described herein in a wide variety of dosage formats, utilizing art-recognized products. See generally, Remington's Pharmaceutical Sciences, (16th ed. 1980). It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known in the medical arts.

In one embodiment, the compounds described herein are administered to a human orally at a dose of about 1 to about 10 mg/kg, about 2 to about 8 mg/kg, or about 4 to about 6 mg/kg of patient body weight. In another embodiment, the daily adult human dose is about 100 to about 1,000 mg, which may be administered qd, bid, tid, and the like. In another embodiment, the daily adult human dose is about 400 to about 600 mg, which may be administered qd, bid, tid, and the like. Such doses may be administered, once, twice, or thrice per day. Illustrative oral unit dosages are 50, 100, 200, and 400 mg (single or divided). Without being bound by theory, it is believed that such illustrative dosages are sufficient to achieve plasma levels of about 1 µg/mL, which may be sufficient to observe bactericidal activity of the compounds described herein, such as for *H. pylori, C. jejuni, Salmonella,* and *Shigella*. It is appreciated that as described herein, the compounds described herein, including CEM-101, reach high concentration in tissues, such as lung tissues. Without being bound by theory, it is believed herein that the compounds described herein, including CEM-101, may achieve tissue levels that are at least about 10-times the MIC for strains, including macrolide-resistant strains, such as but not limited to *H. pylori*, *C. jejuni*, *Salmonella*, and *Shigella*, including organisms that are resistant to macrolides or ketolides, such as AZI, TEL, and/or CLR.

The compounds described herein may be prepared as described herein, or according to US Patent Application Publication No. 2006/0100164 and in PCT International Publication No. WO 2009/055557, the disclosures of which are incorporated herein by reference in their entirety.

Briefly, the synthesis of triazole containing ketolides begins with the known two step preparation of the 12-acyl-imidazole intermediate 4 (Scheme I) from clarithromycin (2). Intermediate 4 is converted into the 11,12-cyclic carbamates 5a-c by the reaction with the corresponding 3-, 4- or 5-carbon linked amino alcohols. Treatment of 5a-c with tosyl chloride provides tosylates 6a-c. Displacement of the tosyl group with NaN$_3$ gives the corresponding azido compounds 7a-c. Cleavage of the cladinose sugar of 7a-c to 8a-8c is accomplished by treatment with HCl in MeOH. Swern oxidation of the 3-hydroxy group of 8a-c gives the corresponding protected ketolides 9a-c which are subsequently deprotected with methanol to afford the required azido ketolides 10a-c, respectively. These azido compounds were reacted with terminally-substituted alkynes in the presence of copper iodide in toluene at 60° C. to regio-selectively afford the corresponding 4-substituted-[1,2,3]-triazoles 11a-18a, 11b-18b, and 11c-18c.

The azide of intermediates 10a-c is converted to the 4-substituted-[1,2,3]-triazoles via a cycloaddition reaction with substituted acetylenes. Triazole rings may be formed via a Huisgen 1+3 cycloaddition reaction between an azide and an alkyne resulting in a mixture of 1,4- and 1,5-regioisomers as depicted in Route A of Scheme II. Alternatively, the procedure of Rostovtsev et al.[8] may be followed using the addition of a CuI catalyst to the reaction to selectively or exclusively produce the 1,4-regioisomer as depicted in Route B of Scheme II.

The triazole ring side chain is also incorporated into the clarithromycin ring system. In one embodiment, a butyl alkyl side chain is chosen. It is appreciated that many butyl side chain analogs in the ketolide series have improved antibacterial activity based on in vitro MIC results. Intermediate 7b is directly converted into the 4-substituted-[1,2,3]-triazole via copper catalyzed cyclization with terminally substituted acetylyenes, as shown in Scheme III. The acetate protecting groups of 19a-e are removed with LiOH in methanol to afford the corresponding 4-substituted-[1,2,3]-triazoles 20a-e.

Substitution of the 2-position hydrogen with a fluorine is accomplished by electrophilic fluorination of 9b (Scheme IV) using Selectfluor®. The azido group of intermediate 22 is converted to a series of 4-substituted-[1,2,3]-triazoles 23a-b via the standard conditions.

Scheme I

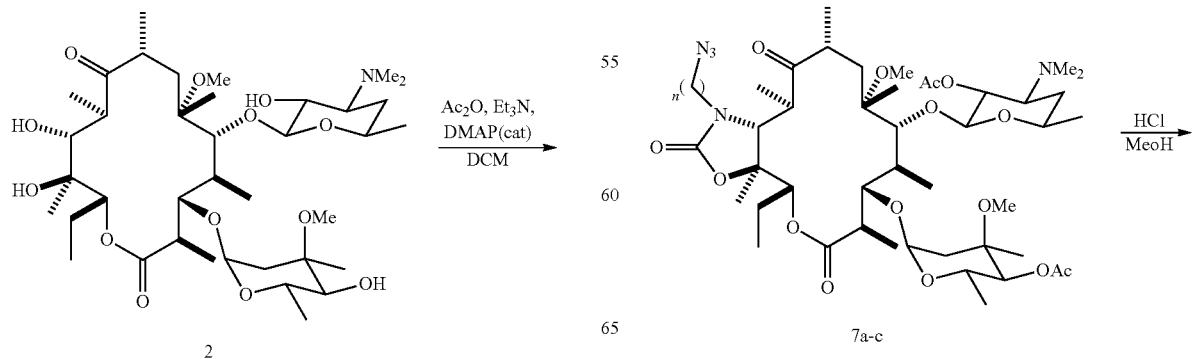

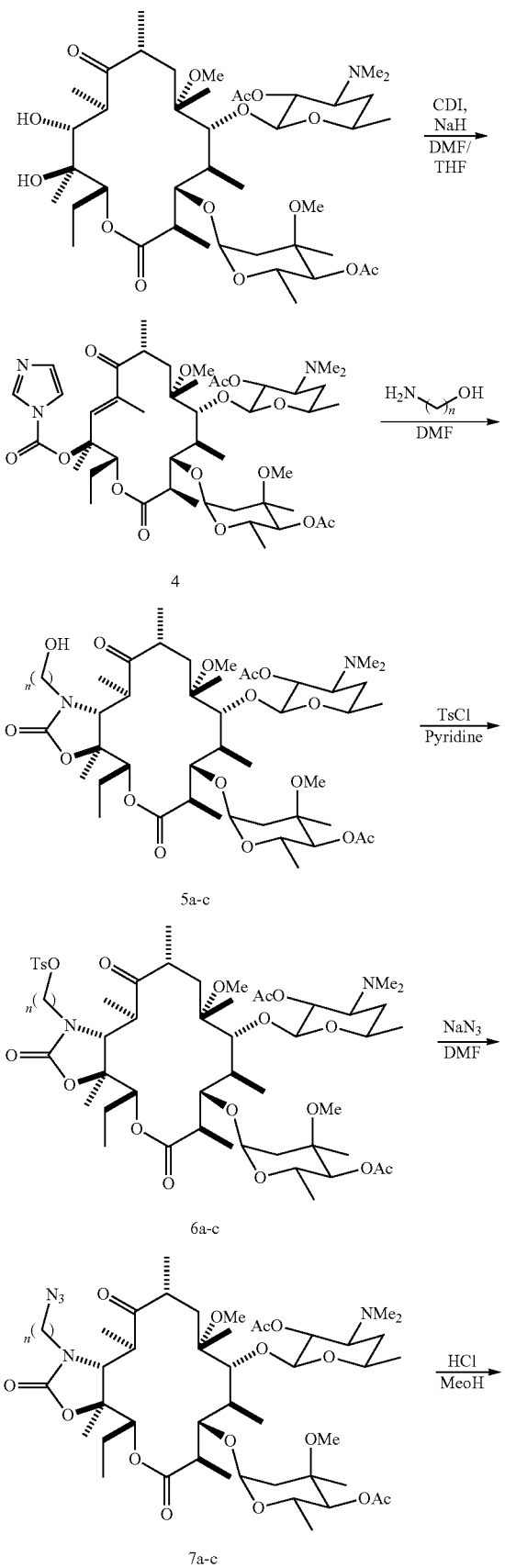

13
-continued
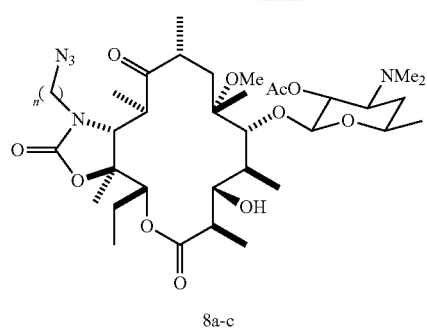
8a-c
14
-continued
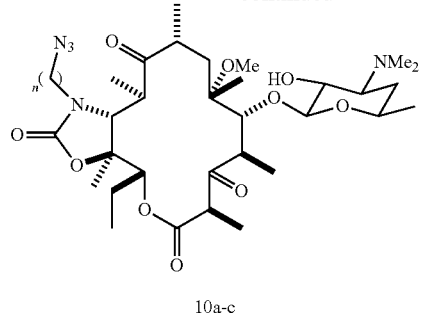
10a-c
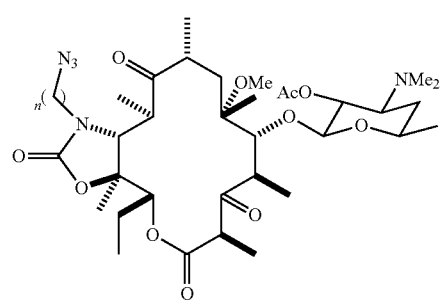
9a-c
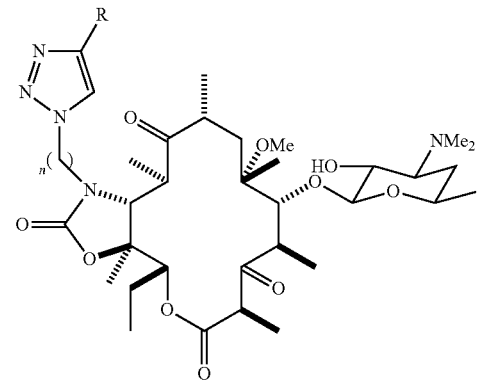
11-18a-c
Scheme II
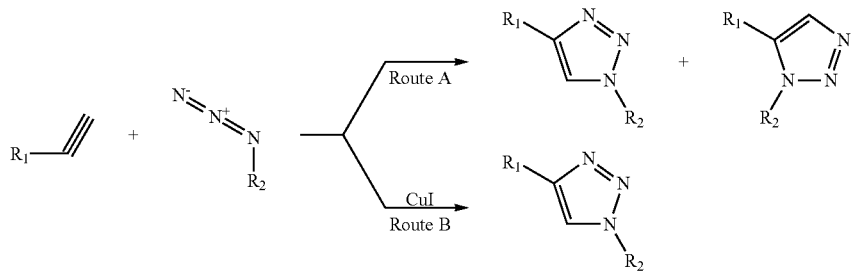
Scheme III
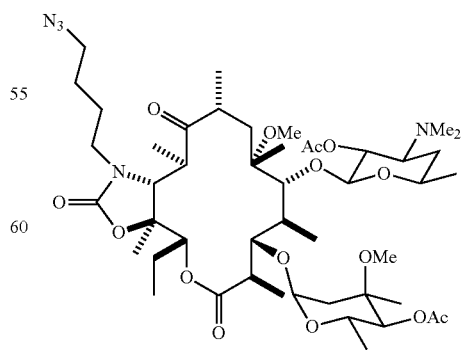
7b 15
-continued
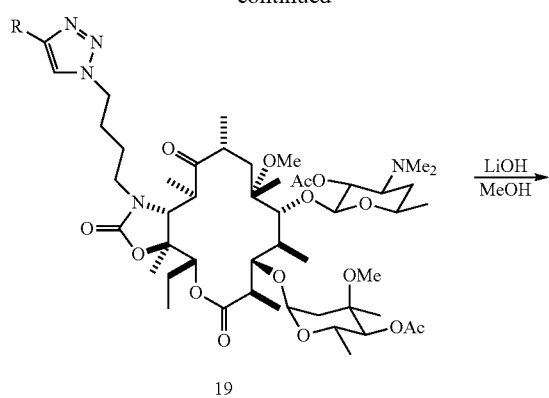
19
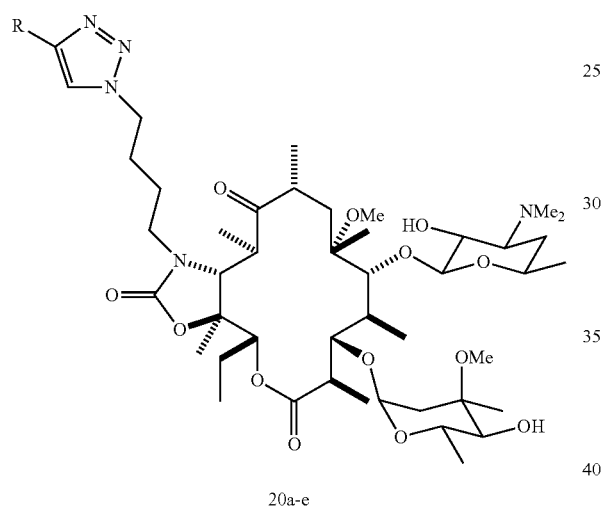
20a-e
Scheme IV
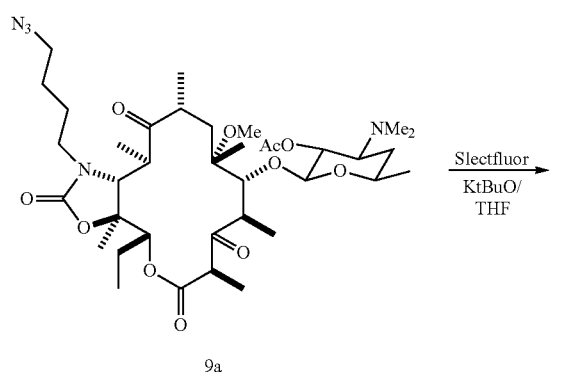
9a
16
-continued
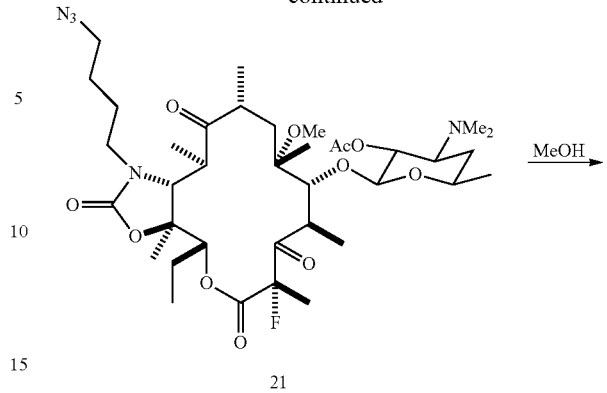
21
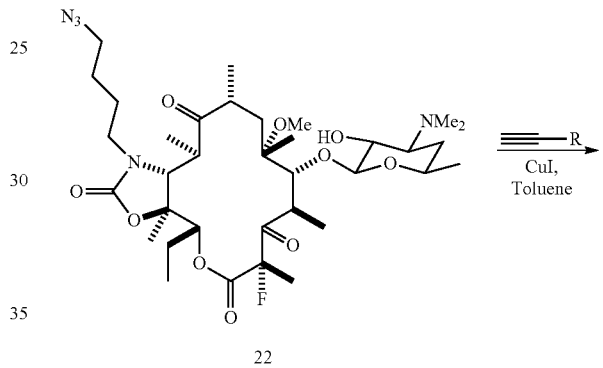
22
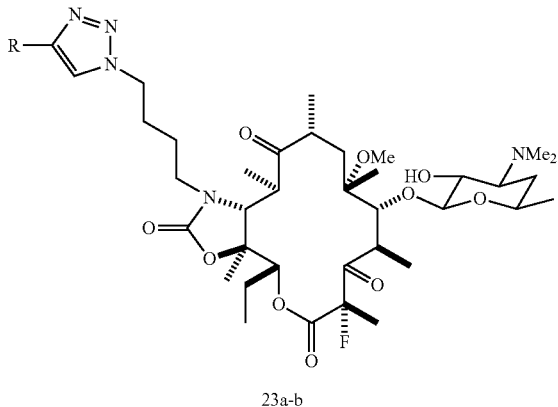
23a-b
In another embodiment, the following compounds are described:

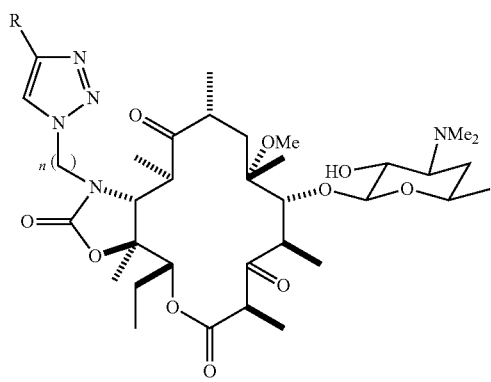
Minimum inhibitory concentration (μg/mL)[a]
| | | | S. aureus | | S. pneumoniae | | | H. influenzae |
|---|---|---|---|---|---|---|---|---|
| | | | | 96:11480 | | | | |
| | | | 29213 | Ery-R | 49619 | 163 | 303 | 49247 |
| Entry | R | n | Ery-S | (MLSb) | Ery-S | Ery-R (MefA) | Ery-R (ermB) | Ery-S |
| TEL | | | ≤0.125 | ≤0.125 | ≤0.125 | ≤0.125 | ≤0.125 | 4 |
| AZI | | | ≤0.125 | >64 | ≤0.125 | >64 | >64 | 2 |
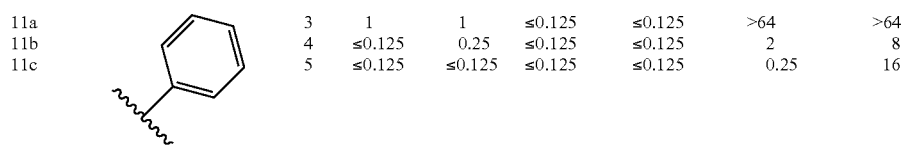
| 11a | | 3 | 1 | 1 | ≤0.125 | ≤0.125 | >64 | >64 |
| 11b | | 4 | ≤0.125 | 0.25 | ≤0.125 | ≤0.125 | 2 | 8 |
| 11c | | 5 | ≤0.125 | ≤0.125 | ≤0.125 | ≤0.125 | 0.25 | 16 |
| 12a | | 3 | 0.25 | 0.5 | ≤0.125 | ≤0.125 | 8 | 64 |
| 12b | | 4 | ≤0.125 | ≤0.125 | ≤0.125 | ≤0.125 | 8 | 8 |
| 12c | | 5 | ≤0.125 | ≤0.125 | ≤0.125 | ≤0.125 | 1 | 16 |
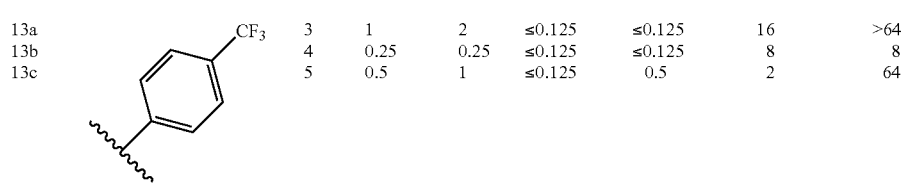
| 13a | | 3 | 1 | 2 | ≤0.125 | ≤0.125 | 16 | >64 |
| 13b | | 4 | 0.25 | 0.25 | ≤0.125 | ≤0.125 | 8 | 8 |
| 13c | | 5 | 0.5 | 1 | ≤0.125 | 0.5 | 2 | 64 |
| 14a | | 3 | 2 | 2 | ≤0.125 | 0.5 | >64 | >64 |
| 14b | | 4 | ≤0.125 | ≤0.125 | ≤0.125 | ≤0.125 | ≤0.125 | 4 |
| 14c | | 5 | ≤0.125 | ≤0.125 | ≤0.125 | ≤0.125 | 0.25 | 64 |

-continued

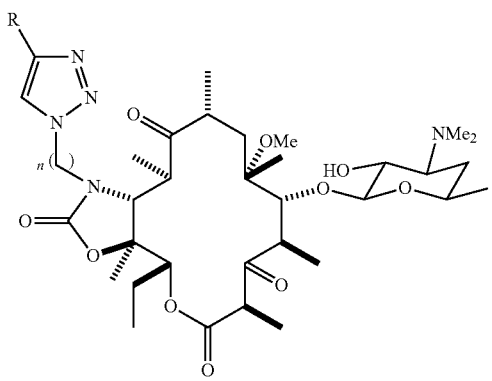

Minimum inhibitory concentration (μg/mL)[a]

| | | | S. aureus | | S. pneumoniae | | | H. influenzae |
|---|---|---|---|---|---|---|---|---|
| | | | 29213 | 96:11480 Ery-R | 49619 | 163 | 303 | 49247 |
| Entry | R | n | Ery-S | (MLSb) | Ery-S | Ery-R (MefA) | Ery-R (ermB) | Ery-S |
| 15a | 3-pyridyl | 3 | 2 | 2 | ≤0.125 | 1 | >64 | >64 |
| 15b | | 4 | ≤0.125 | 4 | ≤0.125 | 2 | 64 | 64 |
| 15c | | 5 | ≤0.125 | 0.25 | ≤0.125 | 0.25 | 4 | 16 |
| 16a | 3-aminophenyl | 3 | 0.5 | nt | ≤0.125 | ≤0.125 | >64 | 16 |
| 16b | | 4 | ≤0.125 | ≤0.125 | ≤0.125 | ≤0.125 | ≤0.125 | 2 |
| 16c | | 5 | ≤0.125 | ≤0.125 | ≤0.125 | ≤0.125 | 0.25 | 8 |
| 17a | 2,6-dichlorophenoxyethyl | 3 | 1 | 1 | ≤0.125 | ≤0.125 | >64 | >64 |
| 17b | | 4 | ≤0.125 | ≤0.125 | ≤0.12 | ≤0.12 | 1 | 16 |
| 17c | | 5 | 0.25 | 0.5 | ≤0.125 | ≤0.125 | 2 | 32 |
| 18a | benzotriazolylethyl | 3 | 1 | 2 | ≤0.125 | 0.5 | >64 | >64 |
| 18b | | 4 | 1 | 2 | ≤0.125 | 4 | 64 | 32 |
| 18c | | 5 | ≤0.125 | ≤0.125 | ≤0.125 | ≤0.125 | 64 | 8 |

[a]National Committee for Clinical Laboratory Standards. Methods for Dilution Antimicrobial Susceptibility Tests for Bacteria that Grow Aerobically, 6th ed.; Approved standard: NCCLS Document M7-A6, 2003.

In another embodiment, the following compounds are described:
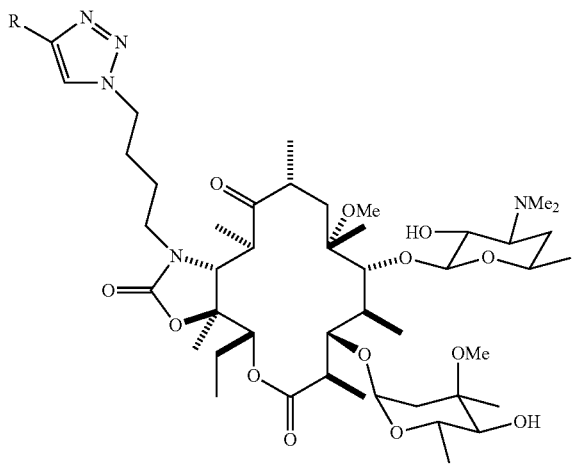
| Entry | R | S. aureus 25923 Ery-S | RN220 | S. pneumoniae 49619 Ery-S | 163 Ery-R (MefA) | 303 Ery-R (ermB) | H. influenzae 49247 Ery-S |
|---|---|---|---|---|---|---|---|
| TEL | | ≤0.25 | 2 | ≤0.125 | ≤0.125 | ≤0.125 | 4 |
| 20a | 2-pyridyl | 0.25 | 8 | ≤0.0625 | 0.125 | 2 | NT |
| 20b | 3-pyridyl | 0.25 | 8 | ≤0.0625 | ≤0.06 | 1 | NT |
| 20c | 3-aminophenyl | 1 | 8 | ≤0.0625 | 0.5 | 2 | NT |
| 20d | 2,6-dichlorophenoxyethyl | 1 | 8 | ≤0.0625 | 0.5 | 2 | NT |
| 20e | benzotriazolylethyl | ≤0.25 | 8 | ≤0.0625 | 0.5 | 2 | NT |

In another embodiment, the following compounds are described:

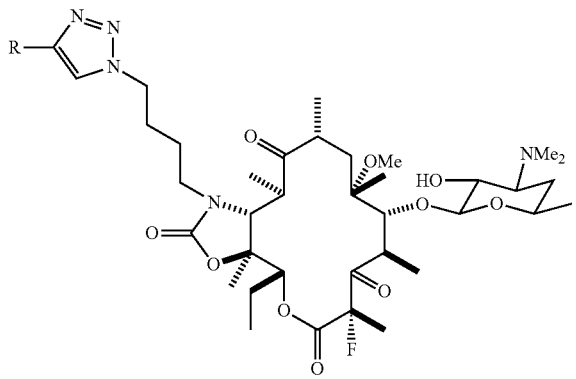

| Entry | R | S. aureus 29213 Ery-S | S. aureus 96:11480 Ery R (MLSb) | S. pneumoniae 49619 Ery-S | S. pneumoniae 163 Ery-R (MefA) | S. pneumoniae 303 Ery-R (ermB) | H. influenzae 49247 Ery-S |
|---|---|---|---|---|---|---|---|
| TEL | | ≤0.125 | ≤0.125 | ≤0.125 | ≤0.125 | ≤0.125 | 4 |
| AZI | | ND | ≤0.125 | >64 | ≤0.125 | >64 | >64 |
| 23a | 2-pyridyl | ≤0.125 | ≤0.125 | ≤0.125 | ≤0.125 | ≤0.125 | 2 |
| 23b (CEM-101) | 3-aminophenyl | ≤0.06 | ≤0.125 | ≤0.125 | ≤0.125 | ≤0.125 | 2 |

In each of the foregoing embodiments, the primary screening panel consisted of relevant *Staph. aureus, S. pyogenes, S. pneumoniae* (including strains resistant to azithromycin and telithromycin). MICs against all pathogens were determined using broth microdilution method as per NCCLS guidelines. Compounds described herein, such as CEM-101 were found to be highly potent having MICs against *S. pneumoniae* (3773) of ≤0.125 μg/mL and *S. pyogenes* (1850) of 0.5 μg/mL, compared to 1 and 8 μg/mL, respectively for Telithromycin. CEM-103 (20c), an analogue of CEM-101 that contains the 3-O-cladinose was found to be less active. Non-heteroaromatic substituted triazole containing ketolides were less active.

The ketolides were tested against erythromycin-sensitive (Ery-S) and erythromycin-resistant (Ery-R) strains of *S. aureus* (29213 (Ery-S) and 96:11480 (Ery-R)), *S. pneumoniae* (49619 (Ery-S) and 163 and 303 (Ery-R)) and *H. influenzae* (49247 (Ery-S)) (Tables 1-3). The broth micro-dilution method was used to determine the Minimum Inhibitory Concentrations (MICs) against all pathogens as per the Clinical and Laboratory Standards Institute (CLSI).

The chain length of the alkyl side chain had a affected activity (Table 1). For example, the 3-carbon linked phenyl substituted triazole 11a was less active against Ery-S and Ery-R *S. aureus* and was inactive against Ery-R *S. pneumoniae* 303 (ermB) a the tested concentrations, whereas the corresponding 4- and the 5-carbon linked phenyl substituted triazoles 11b and 11c were more active against these organisms. A similar trend was observed for the 2-pyridyl substituted triazoles 14a-c, the 3-amino-phenyl substituted triazoles 16a-c, and the 2,5-dichlorophenoxy substituted triazoles 17a-c.

The 4-carbon linked 2-pyridyl substituted triazole 14b and the 3-amino-phenyl substituted triazole 16b possessed the highest potency against *S. pneumoniae* 303, both having MIC values (≤0.125 μg/mL) comparable to telithromycin. The ketolide containing the 4-carbon linked 3-pyridyl substituted triazole 15b was less active against this strain (MIC of 64 μg/mL). Within this series antibacterial activity was improved by extending the carbon linker to 5 atoms, for example the MIC against *S. pneumoniae* 303 for compound 15c improved from 64 to 4 μg/mL. A similar effect was also observed for the benzo-triazole containing ketolide 18c against *S. aureus* but 18c was still inactive against *S. pneumoniae* 303. It is appreciated that a balance between the length of the linker and nature of the aromatic substitution of the triazole may affect the overall activity against macrolide resistant *S. pneumonia* and *S. aureus*.

A correlation between linker length and activity was also observed for *H. influenzae* (49247) where the most potent ketolide series had the substituted triazole linked through either a 4-carbon (11b-14b, 16b, 17b) or a 5-carbon (15c, 18c) chain. Interestingly, the most potent aromatic series against *H. influenzae* was the 3-amino-phenyl with a 3-, 4- or 5-carbon linker (16a, 16b, 16c) having MICs of 16, 2, and 8 µg/mL, respectively, The macrolides containing a cladinose at the 3 position were all highly active against Ery-S *S. pneumoniae* (49619) (Table 2). However, these analogs were less potent than telithromycin against Ery-R strains. The MICs were significantly higher for the cladinose containing analogs with either 2-pyridyl, 2-aminophenyl or 2,6-dichlorophenyl triazole substituents than for the corresponding ketolides (20a, 20c, and 20d versus 14b, 16b, and 17b). Conversely, antibacterial activity was re-established for ketolide analogs 15b (3-pyridyl) and 18b (benzo-triazole) by replacing the keto with the cladinose group in analogs 20b (3-pyridyl) and 20e (benzo-triazole). The MICs improved from 64 µg/mL for 15b and 18b to 1 and 2 µg/mL for 20b and 20e, respectively. A similar activity trend was also observed for Ery-R *S. pneumoniae* 163 (MefA).

COMPOUND EXAMPLES

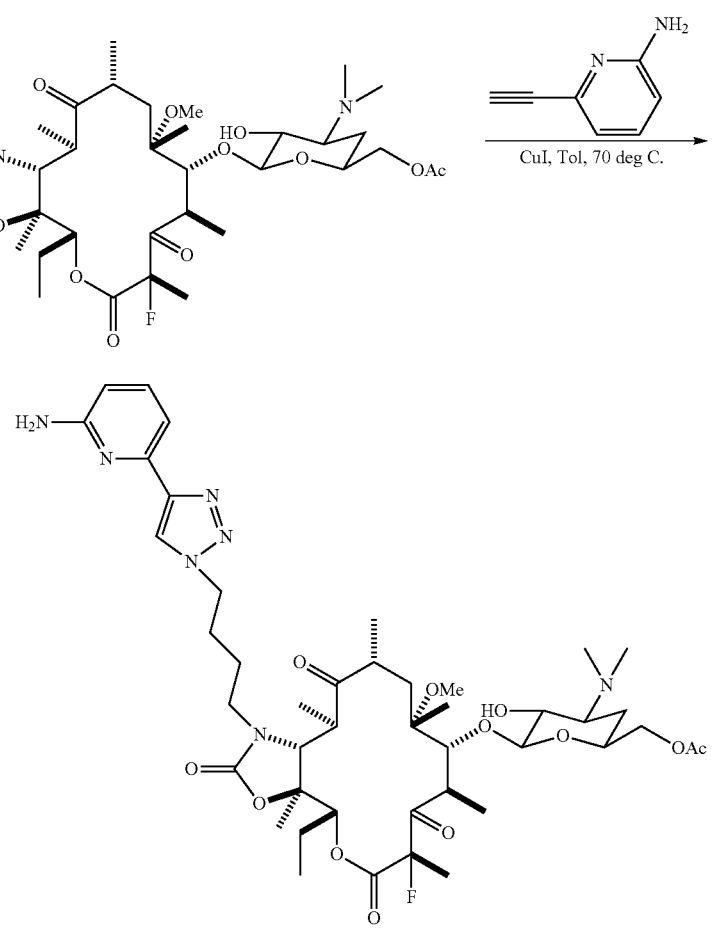

A mixture of 11-N-(4-Azido-butyl)-6-O-methyl-5-(3-dimethylamine-4-deoxy-6-O-acetyl-glu-copyranosyl)-2-fluoro-3-oxo-erythronolide A, 11,12-carbamate (15 mg, 0.019 mmol), 6-Ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, chloroform:methanol plus 1% ammonium hydroxide) to give 14 mg of the desired compound. MS: $C_{44}H_{66}FN_7O_{12}$ calculated $M^+$=903.5. Found: $M+H^+$=904.5.

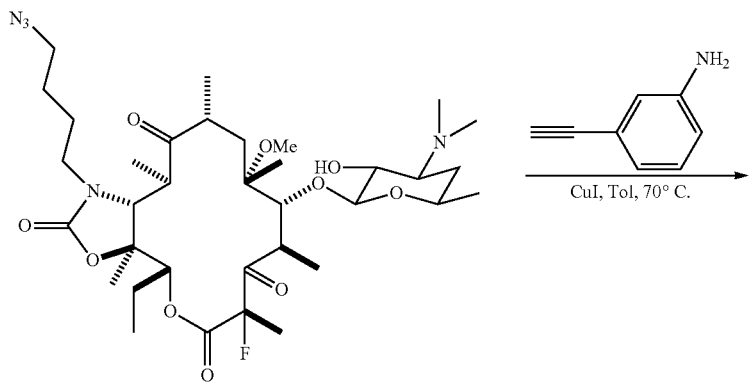

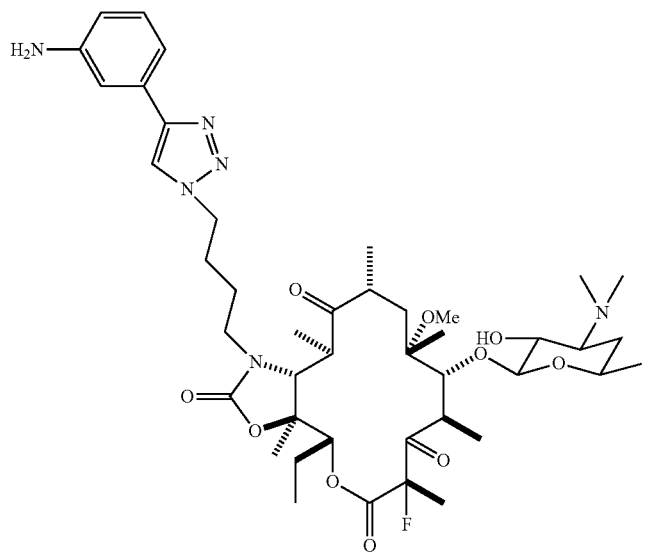

11-N-4-(3-aminophenyl)-[1,2,3]triazol-1-yl]-butyl}-5-desosaminyl-3-oxo-2-fluoro-erythronolide A,-11,12-cyclic carbamate (CEM-101). A mixture of 11-N-(4-azido-butyl)-6-O-methyl-5-desosamynyl-3-oxo-2-fluoro-erythronolide A, 11,12-carbamate (17 mg, 0.023 mmol), 3-Ethynyl-phenylamine (5.4 mg, 0.046 mmol), CuI (1 mg, 0.005 mmol), and toluene (0.2 mL) was heated to 70° C. After 16 h, the mixture was concentrated and directly subjected to silica gel chromatography (9:1, chloroform:methanol plus 1% ammonium hydroxide) to give 17 mg of the desired compound, MS $C_{43}H_{65}FN_6O_{10}$ calculated $M^+$=844.47. Found: $M+H^+$=845.5

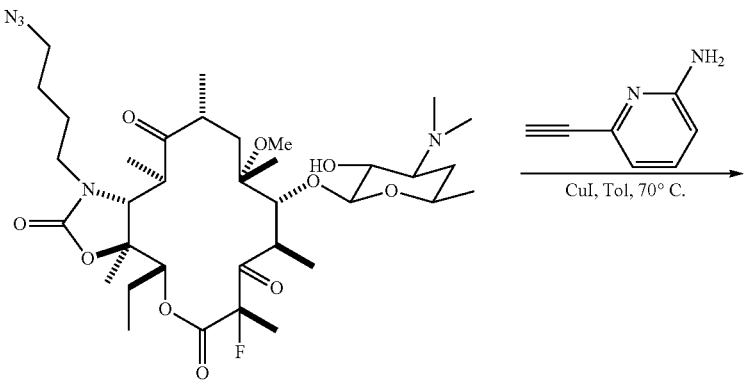

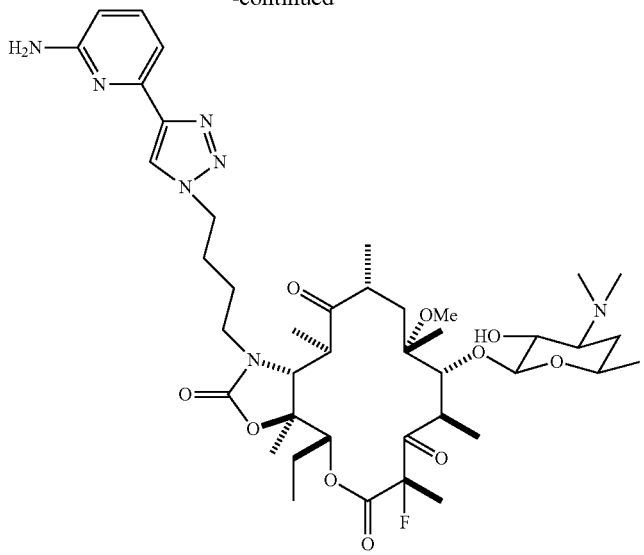

11-N-{4-[4-(6-Amino-pyridin-2-yl)-[1,2,3]triazol-1-yl]-butyl}-5-desosaminyl-3-oxo-2-fluoro-erythronolide A,-11,12-cyclic carbamate. A mixture of 11-N-(4-azido-butyl)-6-O-methyl-5-desosamynyl-3-oxo-2-fluoro-erythronolide A, 11,12-carbamate (15 mg, 0.02 mmol), 6-ethynyl-pyridin-2-ylamine (4.7 mg, 0.4 mmol), CuI (1 mg, 0.005 mmol), and toluene (0.2 mL) was heated to 70° C. After 16 h, the mixture was concentrated and directly subjected to silica gel chromatography (9:1, chloroform:methanol plus 1% ammonium hydroxide) to give 14 mg of the desired compound OP1357. MS: $C_{42}H_{64}FN_7O_{10}$ calculated $M^+=845.5$. Found: $M+H^+=846.5$.

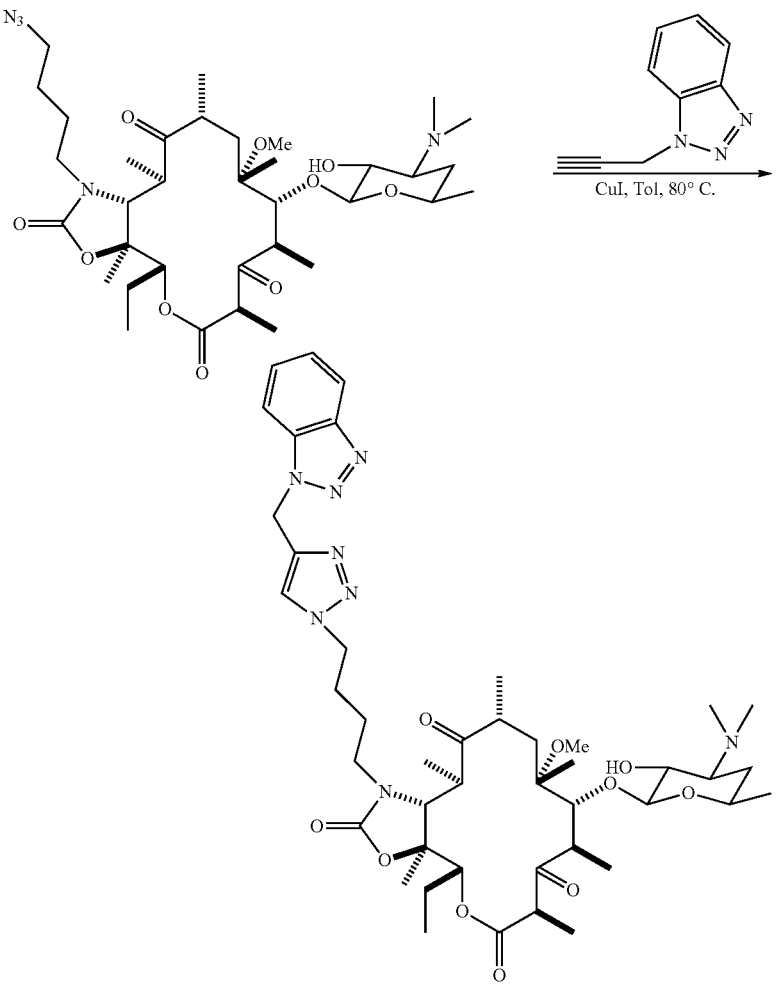

11-N-[4-(4-Benzotriazol-1-ylmethyl-[1,2,3]triazol-1-yl)-butyl]-6-O-methyl-5-O-dasosaminyl-3-oxo-erythronolide A, 11,12-carbamate. A mixture of 11-N-(4-Azido-butyl)-6-O-methyl-5-O-desosaminyl-3-oxo-erythronolide A, 11,12-carbamate (3 mg, 0.0039 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, chloroform:methanol plus 1% ammonium hydroxide) to give 3 mg of the desired compound. MS: $C_{44}H_{66}N_8O_{10}$ calculated $M^+$=866.5. Found: $M+H^+$867.5.

METHOD EXAMPLES

SAL (20 strains, representing 11 serotypes) and *Shigella* (40; four species) were tested by CLSI broth microdilution methods with M100-S18 breakpoints applied. *C. jejuni* (20) and *H. pylori* (23) were tested by Mueller-Hinton agar dilution method, supplemented with sheep blood, and *C. jejuni* results were confirmed by Etest (AB BIODISK, Solna, Sweden). Key comparison agents were tested: AZI, CLR, TEL, levofloxacin (LEV), amoxicillin/clavulanate (A/C) and trimethoprim/sulfamethoxazole (TMP/SMX).

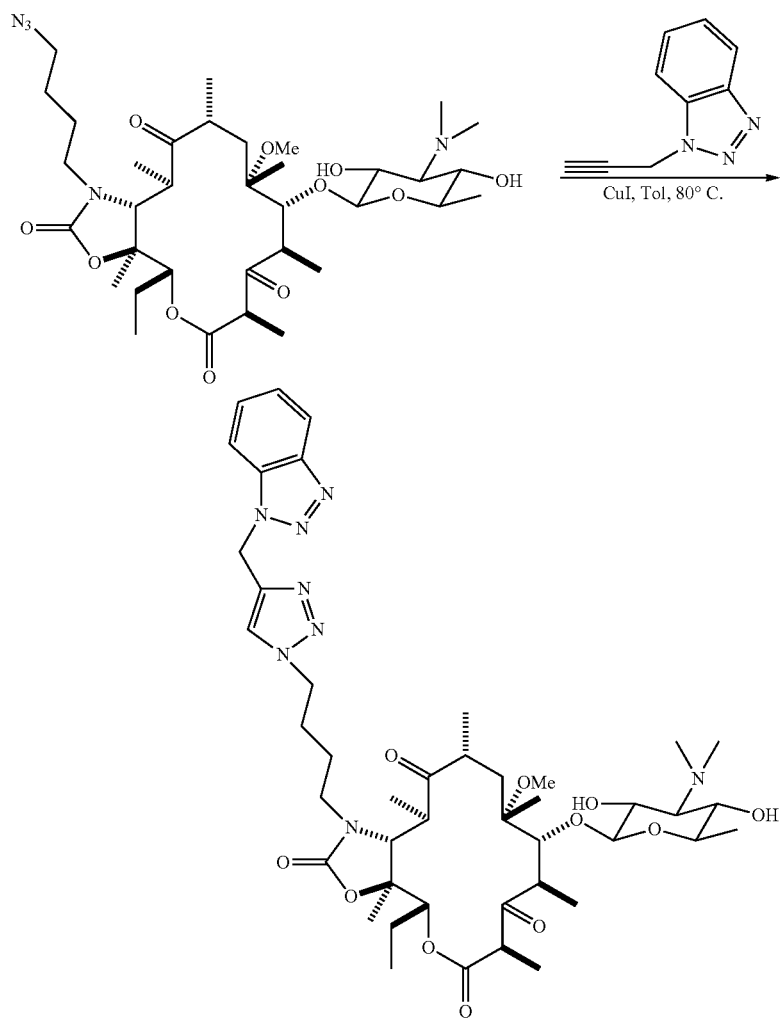

11-N-[4-(4-Benzotriazol-1-ylmethyl-[1,2,3]triazol-1-yl)-butyl]-6-O-methyl-5-mycaminosyl-3-oxo-erythronolide A, 11,12-carbamate. A mixture of 11-N-(4-azido-butyl)-6-O-methyl-5-mycaminosyl-3-oxo-erythronolide A, 11,12-carbamate (3 mg, 0.004 mmol), 1-Prop-2-ynyl-1H-benzotriazole (3 mg, 0.4 mmol), CuI (1 mg, 0.005 mmol), and toluene (0.2 mL) was heated to 80° C. After 16 h, the mixture was concentrated and directly subjected to silica gel chromatography (9:1, chloroform:methanol plus 1% ammonium hydroxide) to give 3 mg of the desired compound. MS: $C_{44}H_{66}N_8O_{11}$ calculated $M^+$=882.5. Found: $M+H^+$=883.5.

CEM-101 demonstrated activity against food-borne GDPs *Salmonella* (MIC50, 4 µg/ml), *Shigella* (MIC50, 8 µg/ml) and *C. jejuni* (MIC50, 1 µg/ml). This was comparable or superior (MIC50 ranges) to: TEL (8-16 µg/ml), ERY (2->4 µg/ml), AZI (4 µg/ml) and A/C (2-8 µg/ml). CLR results were diverse (MIC50 range 0.015->16 µg/ml) as well as were TMP/SMX; LEV was most active (MIC50, ≤0.12 µg/ml). HP CEM-101 MIC results were grouped from 0.03-0.25 µg/ml and at 2 or 4 µg/ml; the latter corresponding to CLA-R (>16 µg/ml) strains.

| | CEM-101 Comparator (drug)[a] | | | | | |
|---|---|---|---|---|---|---|
| | CEM-101 | | | Comparator (drug)[a] | | |
| Organism (no.) | 50% | 90% | Range | 50% | 90% | Range |
| C. jejuni (20) | 1 | 4 | 1-8 | 2 | 4 | 1-8 (CLA) |
| H. pylori (23) | 0.06 | 0.25 | 0.03-4 | 0.03 | 0.12 | ≤0.015->16 (CLA) |
| Salmonella spp. (20) | 4 | >16 | 1->16 | 4 | 8 | 2-8 (AZ) |
| Shigella spp. (40) | 8 | 16 | 1->16 | 4 | 8 | 1->16 (AZ) |

[a]Comparator drug in parentheses (AZI [AZ] or CLR [CLA]).

Some special organism subsets were specifically tested including *Campylobacter jejuni*, *Helicobacter pylori* and Enterobacteriaceae (*Salmonella* spp., *Shigella* spp.). Reference-quality methods were applied including those of the Clinical and Laboratory Standards Institute (CLSI) and the alternative Etest (AB Biodisk, Solna, Sweden) method. In recent years, MLSB-ketolide class compounds have been used for a number of gastrointestinal (GI) infections and resistances to several potential treatment agents requires a search for novel therapeutic options. The compounds described herein were screened in vitro for potential application for these GI indications.

MATERIALS AND METHODS. Susceptibility testing methods: For *C. jejuni*, *N. gonorrhoeae* and *H. pylori*, CLSI M7-A7 (2006) and M100-S18 (2008) agar dilution methods were used as follows: Mueller-Hinton (MH) agar with 5% sheep blood for *H. pylori* and *Campylobacter* spp. 10⁵ CFU/spot inocula. Endpoints read at 24 (*C. jejuni*) or 72 hours (*H. pylori*). Applied incubation environments appropriate for species (added CO2 or microaerophilic).

96-well frozen-form assay panels were also used, produced by JMI Laboratories and consisted of cation-adjusted MH broth for testing the Enterobacteriaceae. Comparator agents were tested Table 1 summarizes CEM-101 activity against *H. pylori*. Eight strains were compared by testing five drugs, including CEM-101. Results showed that CEM-101 was slightly less active than CLR or aminopenicillins (MIC50, ≤0.015 µg/ml); however the comparator activity measurements were Etest results, not the reference agar dilution method. Inter-method data for CLR (data not shown) exhibited a trend toward lower Etest results (four-fold). CEM-101 MICs for the CLR-resistant (>16 µg/ml) strains were only 2 or 4 µg/ml.

TABLE 1

Comparative activity of CEM-101 tested against 103 isolates of enteritis-producing pathogens showing MIC (µg/ml) % by category[a].

| Organism (no. tested), | 50% | 90% | Range | susceptible/resistant |
|---|---|---|---|---|
| *Salmonella* spp. (20)[b] | | | | |
| CEM-101 | 4 | >16 | 1->16 | —/— |
| TEL | 8 | >16 | 0.015->16 | —/— |
| Erythromycin | >4 | >4 | 0.25->4 | —/— |
| CLR | 0.015 | >16 | 0.015->16 | —/— |
| AZI | 4 | 8 | 2-8 | —/— |
| Clindamycin | >4 | >4 | 0.25->4 | —/— |
| Quinupristin-dalfopristin | >4 | >4 | 0.25->4 | —/— |
| Amoxicillin-clavulanate | 2 | 8 | 0.5->8 | 95.0/0.0 |
| Cefdinir | 0.25 | 0.5 | ≤0.12-0.5 | 100.00/0.0 |
| Levofloxacin | ≤0.12 | 1 | ≤0.12-4 | 95.0/0.0 |
| Trim-sulfa[g] | ≤0.25 | ≤0.25 | ≤0.25 | 100.00/0.0 |
| *Shigella* spp. (40)[c] | | | | |
| CEM-101 | 8 | 16 | 1->16 | —/— |
| TEL | 16 | 16 | 2->16 | —/— |
| Erythromycin | >4 | >4 | 0.25->4 | —/— |
| CLR | >16 | >16 | 0.015->16 | —/— |
| AZI | 4 | 8 | 1->16 | —/— |
| Clindamycin | >4 | >4 | 0.25->4 | —/— |
| Quinupristin-dalfopristin | >4 | >4 | >4 | —/— |
| Amoxicillin-clavulanate | 8 | >8 | 2->8 | 72.5/0.0 |
| Cefdinir | 0.25 | 0.25 | ≤0.12-0.5 | 100.0/0.0 |
| Levofloxacin | ≤0.12 | ≤0.12 | ≤0.12-0.25 | 100.0/0.0 |
| Trim-sulfa[g] | >4 | >4 | ≤0.25->4 | 37.5/62.5 |
| *C. jejuni* (20) | | | | |
| CEM-101[d] | 1 | 4 | 1-8 | —/— |
| CLR[e] | 2 | 4 | 1-8 | —/— |
| Ciprofloxacin[e] | 0.25 | >32 | 0.03->32 | —/— |
| Erythromycin[e] | 2 | 4 | 0.5-4 | —/— |
| Tetracycline[e] | 64 | >256 | 0.06-256 | —/— |
| *H. pylori* (23/8)[f] | | | | |
| CEM-101 | 0.06 | 0.25 | 0.03-4 | —/— |
| CLR | 0.03 | 0.12 | ≤0.015->16 | 91.3/8.7 |
| Ampicillin | ≤0.015 | — | ≤0.015-0.03 | —/— |
| Metronidazole | 0.5 | — | 0.06-64 | —/— |
| Tetracycline | 0.06 | — | ≤0.015-0.25 | —/— |

[a]Criteria as published by the CLSI [2008].
— = no interpretational criteria have been established.
[b]Includes: *Salmonella dublin* (1 strain), *S. enteritidis* (4 strains), *S. hadar* (1 strain), *S. heidelberg* (1 strain), *S. infantis* (1 strain), *S. paratyphi* (3 strains), *S. typhi* (3 strains), *S. typhimurium* (1 strain), Group B *Salmonella* (2 strains), Group C *Salmonella* (1 strain), and Group D *Salmonella* (2 strains).
[c]Includes: *Shigella boydii* (6 strains), *dysenteriae* (3 strains), *S. flexneri* (14 strains), and *S. sonnei* (17 strains).
[d]Tested using the agar dilution method recommended by the CLSI (M7-A7).
[e]Tested by Etest using manufacturer's recommendations (AB BIODISK, Solna, Sweden).
[f]Twenty-three were tested by CLSI (2006) method and eight by Etest; ampicillin, metronidazole and tetracycline results were produced by Etest.
[g]Trimethoprim-sulfamethoxazole All organisms to be tested were collected from patients in USA and European medical centers from 2005 to present. Sources of recovered isolates included bloodstream, skin and soft tissue, respiratory tract infections and gastrointestinal tract. Unusual/rare organism species and phenotypes required use of strains isolated prior to 2005 or from other geographic areas. Organisms were tested: *H. pylori* (23; two CLR-resistant), *C. jejuni* (20; fluoroquinolone and tetracycline-resistant samples), *Salmonella* spp. (20; 11 groups), *Shigella* spp. (40; four species).

Table 2 shows the CEM-101 MIC distributions for all tested strains (four species; 103 strains). CEM-101 MIC results for the *H. pylori* were lowest (≤0.03-0.4 µg/ml), while MICs for the Enterobacteriaceae could range up to ≥16 µg/ml.

TABLE 2

| CEM-101 MIC distributions for all tested populations of pathogens in this protocol (103 strains). | | | | | | | | | |
|---|---|---|---|---|---|---|---|---|---|
| Organism (no. tested) | ≤0.03 | 0.06 | 0.12 | 0.25 | 0.5 | 1 | 2 | 4 | 8 | ≥16 |
| H. pylori (23) | 1 | 15 | 2 | 3 | 0 | 0 | 1 | 1 | 0 | 0 |
| C. jejuni (20) | 0 | 0 | 0 | 0 | 0 | 10 | 0 | 8 | 2 | 0 |
| Salmonella spp. (20) | 0 | 0 | 0 | 0 | 0 | 3 | 4 | 4 | 4 | 5 |
| Shigella spp. (40) | 0 | 0 | 0 | 0 | 0 | 2 | 0 | 14 | 18 | 6 |

CEM-101 exhibits potent activity against staphylococci (MIC50, 0.06 µg/ml), streptococci (MIC50, 0.015 µg/ml), enterococci (MIC50/90, 0.25 µg/ml) and other Gram-positive cocci including strains resistant to ERY and CLN. by Etest using manufacturer's package insert directions (AB BIO-DISK). CEM-101 and 14 selected comparison antimicrobial agents were tested.

Quality control (QC) ranges and interpretive criteria for comparator compounds were as published in CLSI M100-S18 (2008); tested QC strains includes S. aureus ATCC 29213, E. faecalis ATCC 29212, S. pneumoniae ATCC 49619, H. pylori ATCC 43504, and C. jejuni ATCC 33560.

CEM-101 inhibited H. pylori (MIC50, 0.06 µg/ml), and various other gastrointestinal pathogens. CEM-101 activity against H. pylori (MIC90, 0.25 µg/ml) was most like that of CLR (MIC90, 0.12 µg/ml). CEM-101 was also most like other macrolides versus C. jejuni (MIC50 and MIC90 results, 1-4 µg/ml). CEM-101 also showed promise for application against intestinal infections caused by Salmonella spp. and Shigella spp., an activity similar to that of AZI.

EXAMPLE. Animal Model of H. pylori Gastroenteritis. Female C57BL/6 mice (age, >7 weeks) are inoculated with the SS1 strain of H. pylori (Lee, et al., 1997, Gastroenterology 112:1386-1397) via gavages of 100-µl suspensions (109 CFU/ml). Infection is monitored (after Crone, et al., Clin Diagn Lab Immunol. 2004 July; 11(4): 799-800) by analyzing fecal pellets using a monoclonal antibody-based enzyme-linked immunosorbent assay (FemtoLab H. pylori Cnx; Connex, Martinsried, Germany) to detect infection by H. pylori (SS1). According to manufacturer's guidelines, an optical density (OD) of <0.150 was defined as negative for H. pylori, and an OD of >0.150 was considered a positive test result.

Infection level and level of gastritis present are also measured using histological methods and culture of tissue homogenates. Mice are sacrificed by $CO_2$ asphyxiation and cervical dislocation, after which the stomachs are excised for histological examination and bacterial culture. Paraffin-embedded sections are stained with hematoxylin and eosin for histology and with a modified May-Grünwald-Giemsa stain to assess bacterial colonization (Laine, et al., 1997, Gastrointest. Endosc. 45:463-467). Gastritis is assessed in the body and the antrum by using a modified Sydney grading system for gastritis (Lee, et al., 1997). The severity of gastritis and bacterial colonization density are assessed blindly by an impartial observer.

CEM-101 is administered with and without a proton pump inhibitor compound according to the dosage regimen in the protocol and the degree of infection monitored as described above.

EXAMPLE. Human THP-1 macrophages were used. Accumulation was measured by microbiological assay. Intracellular activity was determined against phagocytized S. aureus (ATCC 25923; MICs: CEM-101, 0.125 mg/L; AZI, 0.5 mg/L) using a dose-response approach (AAC 2006; 50:841-51). Verapamil (100 µM) and gemfibrozil (250 µM) were used as inhibitors of P-glycoprotein and MRP, respectively (AAC, 2007; 51:2748-57).

Accumulations and activities after 24 h incubation, with and without efflux transporters inhibitors, are shown in the following Table, where Cc/Ce is the apparent cellular to extracellular concentration ratio, and $E_{max}$ is the maximal decrease of intracellular cfu compared to post-phagocytosis inoculum (calculated from non-linear regression [sigmoidal] of dose-effect response experiments).

| | AZI | | | CEM-101 | | |
|---|---|---|---|---|---|---|
| | | Intracellular activity (Δ log cfu at 24 h) | | | Intracellular activity (Δ log cfu at 24 h) | |
| Condition | Cc/Ce[1] (24 h) | Static dose (mg/L) | $E_{max}$[2] | Cc/Ce[1] (24 h) | Static dose (mg/L) | $E_{max}$[2] |
| control | 127.7 ± 23.5 | ~7.0 | 0.10 ± 0.09 | 268.1 ± 7.1 | ~0.02 | −0.85 ± 0.23[b] |
| Verapamil | 216.37 ± 46.6[a] | ~0.2 | −0.37 ± 0.15 | 290.2 ± 12.9 | ~0.03 | −0.59 ± 0.22[b] |
| Gemfibrozil | 129.12 ± 2.69 | ~3.8 | −0.12 ± 0.20 | 308.2 ± 47.8 | ~0.03 | −0.73 ± 0.20[b] |

[a]Statistically significant from both control and Gemfibrozil;
[b]not statistically significant.

EXAMPLE. Intracellular activity of antibiotics. The determination of antibiotic activity against intraphagocytic S. aureus strain ATCC 25923 was determined. Full dose-responses studies were performed to assess the impact of active efflux in the modulation of the intracellular activity of CEM-101 and AZI against intraphagocytic S. aureus (strain ATCC 25923 [MICs: CEM-101, 0.125 mg/L; AZI, 0.5 mg/L]. Antibiotics were compared at 24 h for: (i) their relative static concentration (Cs), and (ii) their relative maximal efficacy (E). While verapamil (but not gemfibrozil) increases the intracellular activity of AZI, neither inhibitor have significant effect on the activity of CEM-101, suggesting that the latter, in contrast with AZI, is not a substrate of the corresponding eukaryotic transporters.

EXAMPLE. Cellular accumulation of antibiotics. The cellular content in macrolides was measured in THP-1 macrophages by microbiological assay, using S. aureus ATCC 25923 as test organism. Cell proteins was assayed in parallel using the Folin-Ciocalteu/Biuret method. The cell associated content in macrolides was expressed by reference to the total cell protein content, and converted into apparent concentrations using a conversion factor of 5 µL per mg of cell protein (as commonly used for cultured cells).

Figure 5:
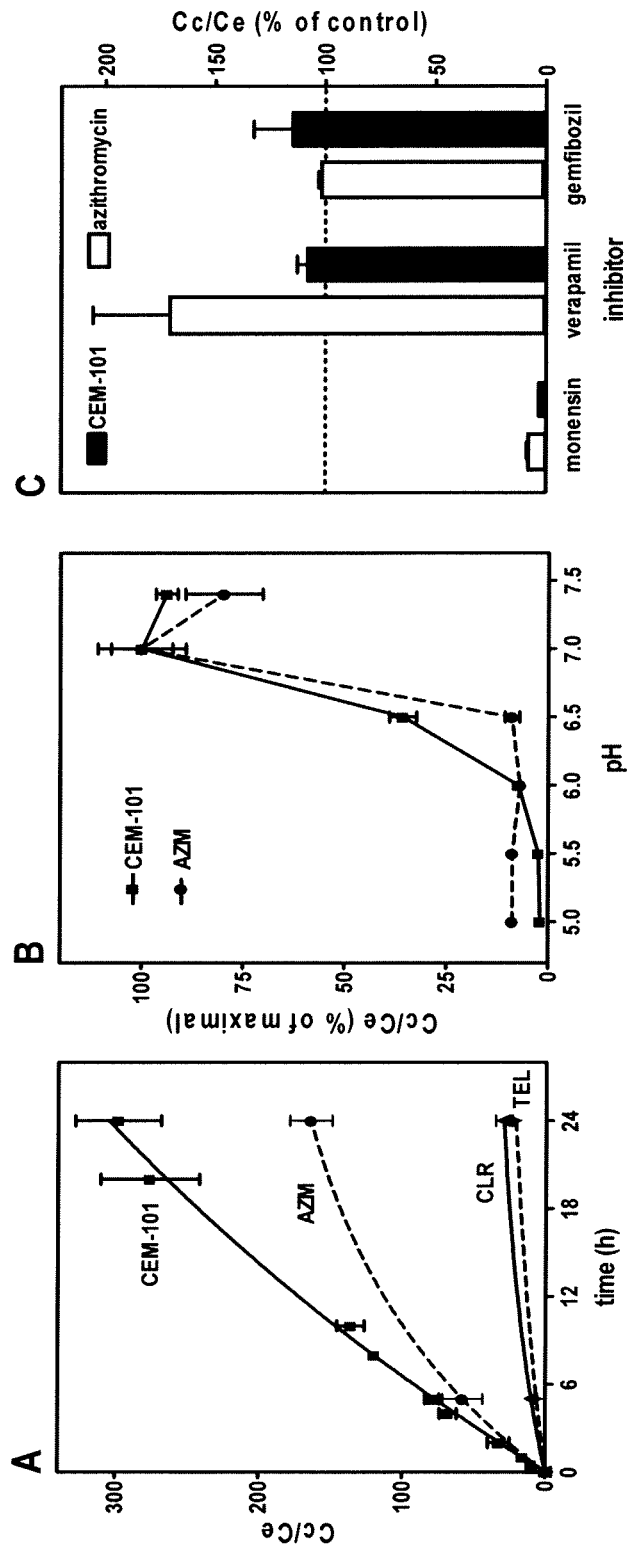
FIG. 5. Accumulation of CEM-101 versus comparators in THP-1 cells at 37° C. (all drugs at an extracellular concentration of 10 mg/liter). (A) Kinetics of accumulation (AZI); Cc, intracellular concentration; Ce, extracellular concentration); (B) influence of the pH of the culture medium on the accumulation (30 min) of CEM-101 (solid symbols and solid line) and AZI (open symbols and dotted line); (C) influence of monensin (50 µM; 2-h incubation), verapamil (150 µM; 24-h incubation), or gemfibrozil (250 µM; 24-h incubation) on the cellular accumulation of AZI and CEM-101. All values are means±standard deviations (SD) of three independent determinations (when not visible, SD bars are smaller than the symbols).

The cellular accumulation of CEM-101 in comparison with that of AZI in THP-1 cells was first measured FIG. 5 (panel A). At 24 h, both antibiotics concentrate to large extents in cells, but with a larger value (Cc/Ce) for CEM-101. In a second stage, whether CEM-101 is a substrate of Pgp or MRP efflux transporters was investigated FIG. 5 (panel B). Using a Pgp (verapamil) or MRPs inhibitor (gemfibrozil), no significant variations of the cellular accumulation of CEM-101 are observed while verapamil increases significantly the cellular accumulation of AZI.

Uptake of CEM-101 was linear over time, reaching accumulation levels about 375-fold within 24 h (AZI, 160X, CLR, 30X, TEL, 21X). Accumulation was suppressed by acid pH or addition of the proton ionophore monensin, but not modified by verapamil or gemfibrozil (preferential inhibitors of Pgp and MRP, respectively). Panel B shows that the accumulation of both CEM-101 and AZI was reduced when the experiments were conducted at acidic pH, with the change occurring almost entirely when the pH was brought from 7 to 6. Panel C shows that monensin, which is known to decrease the cellular accumulation of many weak organic bases, also almost completely suppressed the accumulation of both CEM-101 and AZI. In contrast, verapamil, an inhibitor of the P-glycoprotein efflux transporter (Pgp, also known as MDR1), increased the accumulation of AZI without affecting that of CEM-101, whereas gemfibrozil, an inhibitor of multidrug resistance proteins (MRP) and other organic anion transporters did not affect either compound. Neither verapamil nor gemfibrozil affected the accumulation of TEL or CLR (data not shown). The efflux of CEM-101 from cells incubated with 10 mg/L of CEM-101 for 1 h and then transferred into drug-free medium was examined. Efflux proceeded in a bimodal fashion, with half of the cell-associated drug being released within approximately 10 min, followed by a slower release phase of several hours (data not shown).

EXAMPLE. Macrolides accumulate in eukaryotic cells and are considered advantageous for the treatment of intracellular infections. Ketolides are active against erythromycin-resistant organisms. The cellular accumulation and intracellular activity of CEM-101 towards the intracellular forms of *Staphylococcus aureus* (S. a.), *Listeria monocytogenes* (L. m.), and *Legionella pneumophila* (L. p.) in comparison with AZI, CLR, and TEL is shown in the following table.

| | MIC$^a$ | Cs$^b$ | E$_{max}$$^c$ |
|---|---|---|---|
| CEM-101 | | | |
| S.a. | 0.06 | 0.022 | −0.86 |
| L.m. | 0.004 | 0.11 | −0.66 |
| L.p. | 0.004 | 0.018 | −1.03 |
| AZI | | | |
| S.a. | 0.5 | >50 | 0.04 |
| L.m. | 1 | 11.6 | −0.81 |
| L.p. | 0.016 | 2.90 | −0.83 |
| CLR | | | |
| S.a. | 0.5 | 0.84 | −0.18 |
| L.m. | | | |
| L.p. | 0.007 | 0.12 | −0.71 |
| TEL | | | |
| S.a. | 0.25 | 0.63 | −0.29 |
| L.m. | | | |
| L.p. | 0.007 | 0.06 | −0.63 |

$^a$mg/L;
$^b$static concentration (mg/L) at 24 h;
$^c$Δ log$_{10}$ CFU at 24 h compared to the post-phagocytosis inoculum EXAMPLE. MICs and extracellular activities of antibiotics were determined in MHB at both neutral and acidic pH. Intracellular activity was determined against *S. aureus* (ATCC 25923) phagocytosed by THP-1 macrophages as previously described (AAC, 2006, 50:841-851). Results were expressed as a change of efficacy compared to time 0 h.

| Conditions | CEM-101 | AZI | CLR | TEL |
|---|---|---|---|---|
| MICs (mg/L) | | | | |
| (i) pH 7.4 | 0.125 | 0.5 | 0.5 | 0.5 |
| (ii) pH 5.5 | 1-2 | 256 | 16 | 8 |
| Extracellular activity (24 h): Δ log cfu from time 0 h | | | | |
| (i) Broth pH 7.4 | | | | |
| Emax$^1$ | −1.4 ± 0.1 | −1.2 ± 0.6 | −1.4 ± 0.2 | −1.0 ± 0.4 |
| Static dose$^2$ | ~0.06 | ~3.63 | ~1.41 | ~0.28 |
| R$^2$ | 0.964 | 0.860 | 0.965 | 0.868 |
| (ii) Broth pH 5.5 | | | | |
| Emax$^1$ | −1.6 ± 0.4 | +2.1 ± 0.1 | −1.5 ± 0.8 | −1.4 ± 0.9 |
| Static dose$^2$ | ~1.48 | / | ~10.47 | ~9.33 |
| R$^2$ | 0.915 | / | 0.911 | 0.879 |
| Intracellular activity (24 h): Δ log cfu from time 0 h | | | | |
| Emax$^1$ | −0.8 ± 0.2 | 0.10 ± 0.0 | −0.1 ± 0.1 | −0.4 ± 0.2 |
| Static dose$^2$ | ~0.02 | ~7.8 | ~0.98 | ~0.23 |
| R$^2$ | 0.906 | 0.980 | 0.974 | 0.935 |
| THP-1 | | | | |
| Emax$^1$ | −0.8 ± 0.2 | 0.1 ± 0.1 | −0.1 ± 0.1 | −0.4 ± 0.1 |
| Static dose$^2$ | ~0.02 | ~10 | ~0.98 | ~0.28 |

$^1$Maximal decrease of intracellular cfu compared to initial, post-phagocytosis inoculum (calculated from non-linear regression [sigmoidal] of dose-effect response) run in broth (extracell.) or with infected macrophages (intracell.)
$^2$Extracellular concentration (Cs in mg/L) yielding an apparent static effect. Comparative pharmacological descriptors (Emax and static concentrations [Cs]) obtained from the dose-responses studies. Dose-response studies in Mueller-Hinton broth. Against *S. aureus* ATCC 25923 and in broth, at pH 7.4, CEM-101 is systematically more active than AZI, CLR and TEL; at pH 5.5, AZI, CLR and TEL show significant decrease of their potencies, while CEM-101 shows less change.

Compared to AZI, CLR and TEL, CEM-101 activity was less affected by acidic pH of the broth and showed greater potency (lower static dose) and larger maximal efficacy (Emax) against intracellular *S. aureus*.

EXAMPLE. Cell lines. Experiments were performed with THP-1 cells (ATCC TIB-202; American Tissue Culture Collection, Manassas, Va.), a human myelomonocytic cell line displaying macrophage-like activity (see, e.g., Barcia-Macay et al., Antimicrob. Agents Chemother. 50:841-851 (2006)). Assay of the cell-associated macrolides and calculation of the apparent cellular- to-extracellular-concentration ratios. Macrolides were assayed by a microbiological method, using *S. aureus* ATCC 25923 as a test organism. Cell proteins were measured in parallel using the Folin-Ciocalteu/biuret method. The cell-associated contents in macrolides were expressed by reference to the total cell protein content and converted into apparent concentrations using a conversion factor of 5 µL per mg of cell protein, an average value found for many cultured cells.

Bacterial strains, susceptibility testing, and 24-h dose-response curve studies with broth. *S. aureus* ATCC 25923 (methicillin [meticillin] sensitive), *L. monocytogenes* strain EGD, and *L. pneumophila* strain ATCC 33153 were used in the present study. MIC determinations were performed in Mueller-Hinton broth (for *S. aureus*) and tryptic soy broth (for *L. monocytogenes*) after a 24-h incubation, or in α-ketoglutarate-buffered yeast extract broth (for *L. pneumophila*) after a 48-h incubation. For *S. aureus* studies, 24-h concentration-response experiments in acellular medium were performed in Mueller-Hinton broth.

Cell infection and assessment of antibiotic intracellular activities. Infection of THP-1 cells and assessment of the intracellular activity of antibiotics were performed using conventional methods for *S. aureus* and *L. monocytogenes* or with minor adaptations for *L. pneumophila* using (i) a multiplicity of infection of 10 bacteria per macrophage and (ii) gentamicin (50 mg/liter) for 30 to 45 min for the elimination of nonphagocytosed bacteria.

Statistical analyses. Curve-fitting statistical analyses were performed with GraphPad Prism version 4.03 and GraphPad Instat version 3.06 (GraphPad Software, San Diego, Calif.).

EXAMPLE. Susceptibility toward *S. aureus* ATCC 25923, *Listeria monocytogenes* EGD, and *Legionella pneumophila* ATCC 33153. CEM-101 showed lower MICs than AZI against the three selected organisms (*S. aureus*, 0.06 and 0.5 mg/liter; *L. monocytogenes*, 0.004 and 1 mg/liter; and *L. pneumophila*, 0.004 and 0.016 mg/liter) in conventional susceptibility testing. The MICs of CEM-101, TEL, AZI, and CLR against *S. aureus* and *L. monocytogenes* were measured in broths adjusted to pH values ranging from 5.5 to 7.4. The range was selected to cover the values at which the antibiotics could be exposed in the extracellular milieu or intracellularly for the two organisms considered. As illustrated in FIG. 1, all four drugs showed a marked decrease in potency against both organisms when the pH was decreased from 7.4 to 5.5, with AZI demonstrating the most significant loss of activity. CEM-101 retained the most activity, consistently showing the lowest MICs throughout the entire pH range investigated, with values (mg/liter) ranging from 0.06 (pH 7.4) to 0.5 (pH 5.5) for *S. aureus* (ATCC 25923) and 0.0039 (pH 7.4) to 0.25 (pH 5.5) for *L. monocytogenes* (EDG). For *L. pneumophila* (data not shown), the MIC of CEM-101 increased from 0.005 to 0.01 and that of AZI from approximately 0.01 to 0.25 mg/liter when the pH of the broth was decreased from 7.4 to 6.5 (no determination could be made at lower pH values because of absence of growth).

Figure 3:
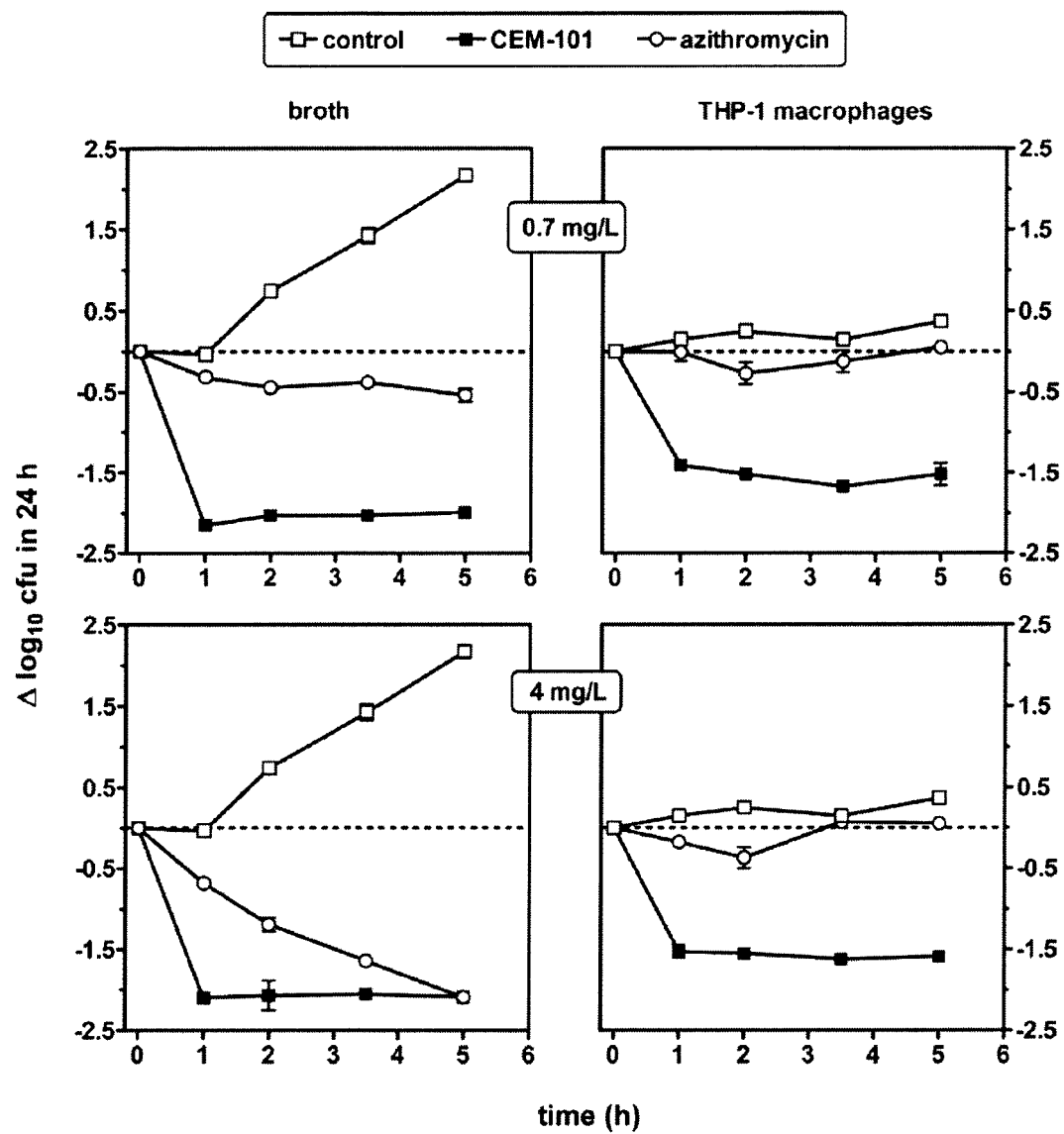
FIG. 3. Concentration-effect relationships for CEM-101, TEL, CLR, and AZI toward *S. aureus* (ATCC 25923) in broth (left panels) and after phagocytosis by THP-1 macrophages (right panels). The ordinate shows the change in CFU (Δ log CFU) per ml (broth) or per mg of cell protein (THP-1 macrophages) at 24 h compared to the initial inoculum. The abscissa shows the concentrations of the antibiotics as follows: (i) top panels, weight concentrations (in mg/liter) in broth (left) or in the culture medium (right) and (ii) bottom panels, multiples of the MIC as determined in broth at pH 7.4. All values are means±standard deviations (SD) of three independent experiments (when not visible, SD bars are smaller than the symbols). Statistical analysis based on global analysis of curve-fitting parameters (one-way analysis of variance); the only significant difference is between CEM-101 and AZI in broth (P=0.04). Numerical values of the pertinent pharmacological descriptors and statistical analysis of their differences are shown in Table 1.

EXAMPLE. Time and concentration effects against extracellular and intraphagocytic *S. aureus*. Short-term (6-h) time-kill curves were obtained for CEM-101 in comparison with those for AZI against *S. aureus* (ATCC 25923) in broth and after phagocytosis by THP-1 macrophages using two single fixed concentrations of 0.7 and 4 mg/liter. The lower concentration was chosen to be relevant to the serum concentration of AZI and CEM-101, and the higher concentration was selected to be above the MIC of AZI for the organisms of interest. Results presented in FIG. 3 show that under these conditions, only CEM-101 was able to significantly decrease CFU in broth as well as in THP-1 macrophages at the 0.7-mg/liter concentration. At the 4-mg/liter concentration in broth, AZI eventually achieved the same antibacterial effect as CEM-101, but at a lower rate (5 h compared to 1 h). In THP-1 macrophages, no consistent activity was detected for AZI, even at the 4-mg/liter concentration, whereas CEM-101 again achieved a reduction of approximately 1.5 log 10 CFU, similar to the magnitude seen at the 0.7-mg/liter concentration. In all situations with CEM-101, the maximal decrease of CFU was obtained within 1 h and was maintained thereafter.

Figure 2:
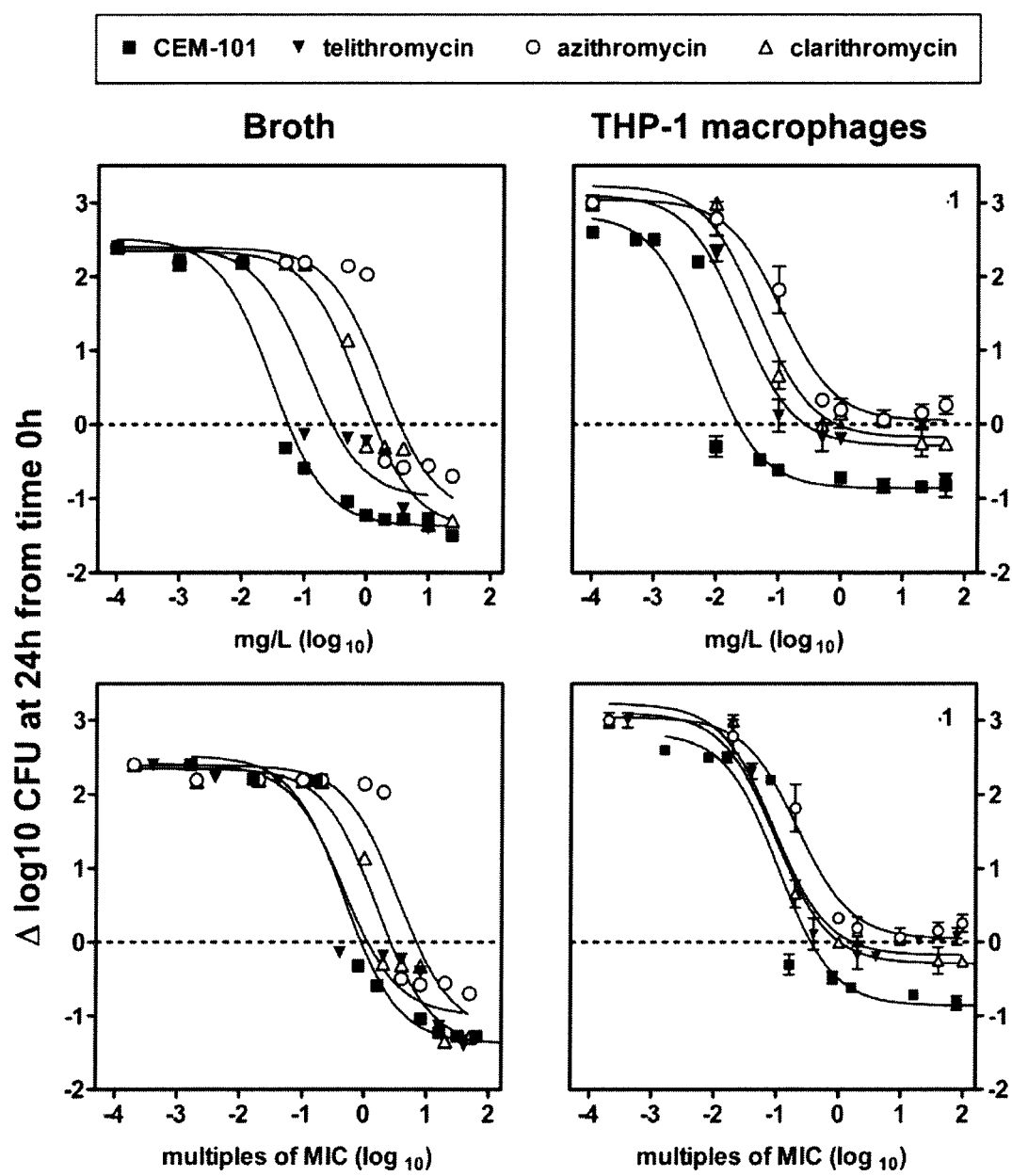
FIG. 2. Short-term time-kill effect of CEM-101 and AZI on *S. aureus* (ATCC 25923) in broth (left panels; pH 7.4) or after phagocytosis by THP-1 macrophages (right panels). Both drugs were used at an extracellular concentration of either 0.7 (top panels) or 4 (bottom panels) mg/liter. MICs of CEM-101 and AZI were 0.06 and 0.5 mg/liter, respectively. All values are means±standard deviations (SD) of three independent experiments (when not visible, SD bars are smaller than the symbols).

We then performed concentration-response experiments at a fixed time point (24 h) to obtain the pertinent pharmacological descriptors of CEM-101 activity (relative potency [50% effective concentration {EC50}], apparent static concentration [$C_s$], and relative maximal efficacy [$E_{max}$] in comparison with CLR, AZI and TEL activity (additional details are described in Barcia-Macay et al., Pharmacodynamic evaluation of the intracellular activities of antibiotics against *Staphylococcus aureus* in a model of THP-1 macrophages Antimicrob. Agents Chemother. 50:841-851 (2006)). Data are presented in FIG. 2 as a function of (i) weight concentrations (mg/liter) and (ii) multiples of the MICs (as determined in broth at pH 7.4). The numerical values of the corresponding pharmacological descriptors are shown in the Table. Pertinent regression parameters[a] (with confidence intervals [C1]), and statistical analysis of the dose-response curves illustrated in FIG. 2.

| antibiotic | $E_{max}$◆ (CI) | | broth+ $EC_{50}$◇ (CI) | $C_S$◇◇ | $R^2$ |
|---|---|---|---|---|---|
| CEM-101 | −1.37 | mg/L | 0.03 | 0.06 | 0.973 |
| | (−1.67 to −1.08) | | (0.02 to 0.06) | | |
| | a; A | | a; A | | |
| | | x MIC | 0.48 | 0.88 | |
| | | | (0.26 to 0.91) | | |
| | | | a; A | | |
| TEL | −1.00 | mg/L | 0.12 | 0.29 | 0.892 |
| | (−1.78 to −0.22) | | (0.03 to 0.52) | | |
| | a; A | | b; A | | |
| | | x MIC | 0.46 | 0.96 | |
| | | | (0.11 to 2.06) | | |
| | | | a; A | | |
| AZI | −1.23 | mg/L | 1.78 | 3.4 | 0.872 |
| | (−2.55 to 0.083) | | (0.45 to 7.02) | | |
| | a; A | | c; A | | |
| | | x MIC | 3.55 | 6.87 | |
| | | | (0.90 to 14.0) | | |
| | | | b; A | | |

-continued

| | | | | | |
|---|---|---|---|---|---|
| CLR | −1.41<br>(−1.95 to −0.87)<br>a; A | mg/L | 0.80<br>(0.41 to 1.56)<br>c; A | 1.32 | 0.956 |
| | | x MIC | 1.59<br>(0.81 to 3.1)<br>a, b; A | 2.65 | |

| | | THP-1 macrophages[++] | | | |
|---|---|---|---|---|---|
| antibiotic | $E_{max}$[♦] (CI) | | $EC_{50}$[◊] (CI) | $C_s$[◊◊] | $R^2$ (CI) |
| CEM-101 | −0.86<br>(−1.36 to −0.37)<br>a; B | mg/L | 0.0068<br>(0.0023 to 0.020)<br>a; B | 0.022 | 0.927 |
| | | x MIC | 0.11<br>(0.037 to 0.32)<br>a; B | 0.35 | |
| TEL | −0.29<br>(−0.70 to 0.12)<br>b; B | mg/L | 0.024<br>(0.007 to 0.088)<br>b; B | 0.63 | 0.954 |
| | | x MIC | 0.097<br>0.027 to 0.35<br>a; B | 1.04 | |
| AZI | 0.04<br>(−0.23 to 0.32)<br>b; B | mg/L | 0.11<br>(0.05 to 0.22)<br>c; B | >50 | 0.983 |
| | | x MIC | 0.22<br>0.11 to 0.45<br>a; B | >100 | |
| CLR | −0.18<br>(−0.52 to 0.16)<br>b; B | mg/L | 0.046<br>(0.018 to 0.12)<br>b, c; B | 0.84 | 0.974 |
| | | x MIC | 0.093<br>0.035 to 0.25<br>a; B | 1.68 | |

Figure 4:
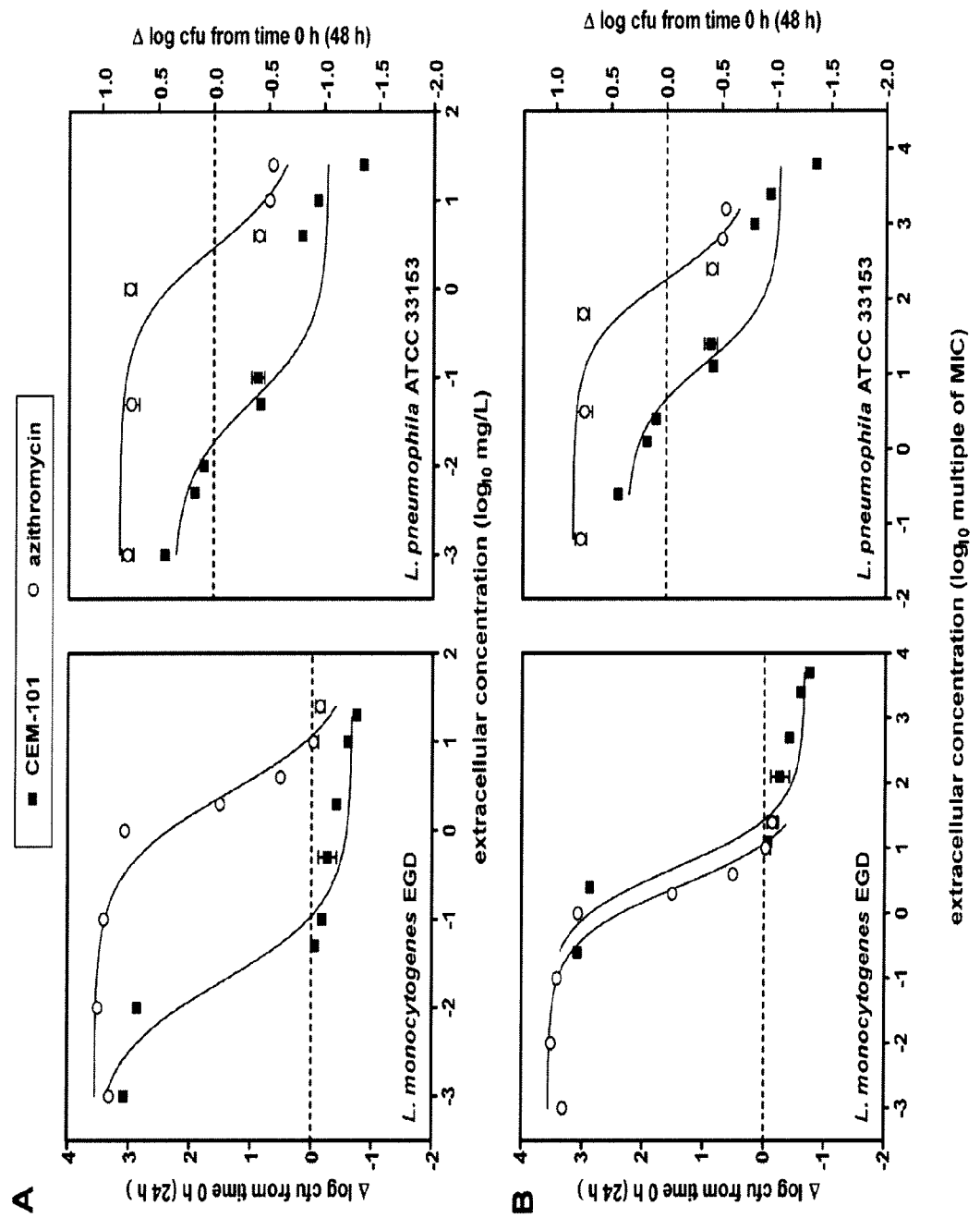
FIG. 4. Concentration-effect relationships for CEM-101 and AZI toward intraphagocytic *L. monocytogenes* (strain EGD, left panels) and *L. pneumophila* (strain ATCC 33153, right panels). The ordinate shows the change in CFU (Δ log CFU) per mg of cell protein at 24 h (*L. monocytogenes*) or 48 h (*L. pneumophila*) compared to the initial postphagocytosis inoculum. The abscissa shows the concentrations of the antibiotics as follows: (i) top panels, weight concentrations (in mg/liter); (ii) bottom panels, multiples of the MIC as determined in broth at pH 7.4. All values are means±standard deviations (SD) of three independent experiments (when not visible, SD bars are smaller than the symbols).

[a]using all data points shown in FIG. 4 (data from samples without antibiotic when the extracellular concentration of an antibiotic is lower than 0.01 x MIC (5)
[+]original inoculum [time = 0 h]: 0.97 ± 0.24 × $10^6$ CFU/mL (n = 3)
[++]original (post-phagocytosis) inoculum [time = 0 h]: 2.74 ± 0.55 × $10^6$ CFU/mg protein (n = 3)
[♦]CFU decrease (in $log_{10}$ units) at time = 24 h from the corresponding original inoculum, as extrapolated for antibiotic concentration = ∞; samples yielding less than 5 counts were considered below detection level.
[◊] concentration (in mg/L or in x MIC) causing a reduction of the inoculum half-way between initial ($E_0$) and maximal ($E_{max}$) values, as obtained from the Hill equation (using a slope factor of 1);
[◊◊] concentration (in mg/L or in x MIC) resulting in no apparent bacterial growth (number of CFU identical to the original inoculum), as determined by graphical intrapolation; Statistical Analyses. Analysis of the differences between antibiotics (per column for the corresponding rows; one-way ANOVA with Tuckey test for multiple comparisons between each parameter for all drugs): figures with different lower case letters are significantly different from each other (p < 0.05). Analysis of the differences between broth and THP-1 macrophages (per row for the corresponding columns; unpaired, two-tailed t-test): figures with different upper case letters are significantly different from each other (p < 0.05).

The activities in both broth and THP-1 macrophages developed in a concentration-dependent fashion, as denoted by the sigmoidal shape of each best-fit function (Hill equation). In broth, the relative efficacy of CEM-101 ($E_{max}$ of −1.37 $log_{10}$) was similar to that of the other drugs ($E_{max}$ values of −1.00 to −1.41 $log_{10}$). In THP-1 macrophages, the relative efficacy of CEM-101 was significantly decreased compared to that in broth ($E_{max}$ of −0.86 $log_{10}$), but not to the same extent as those of the other drugs, which essentially became bacteriostatic only ($E_{max}$ values of 0.04 to −0.29 $log_{10}$). On a weight basis, CEM-101 had higher relative potencies (lower $E_{50}$ values) and lower static concentrations (lower $C_s$ values) than all three comparator drugs in both broth and in THP-1 macrophages. When the data were analyzed as a function of equipotent concentration (multiples of the MIC), these differences in $EC_{50}$ values were reduced, indicating that the MIC was the main driving parameter in this context. In broth, even when analyzed as multiples of the MIC, CEM-101 and CLR still showed significantly lower $EC_{50}$s than TEL and AZI.

Example. Activity against intraphagoctic *L. monocytogenes* and *L. pneumophila*. The same approach was used as that for *S. aureus* to assess the activities of CEM-101 and AZI against phagocytized *L. monocytogenes* and *L. pneumophila* to obtain information on concentration-effect relationships and on the corresponding pertinent pharmacological descriptors. As shown in FIG. 4, a relationship compatible with the Hill equation was observed in all cases, although the limited growth of *L. pneumophila* made the fitting of functions somewhat more uncertain. When the data were plotted against weight concentration, it appeared that CEM-101 had a higher relative potency (lower EC50) than AZI for both *L. monocytogenes* and *L. pneumophila*. This difference was reduced but nevertheless remained significant when data for *L. pneumophila* were plotted against multiples of the MIC, indicating that the MIC was an important but not the exclusive driver of intracellular activity against this organism. Conversely, no difference in the responses was seen for *L. monocytogenes* when data were expressed as multiples of the MIC. Numerical values of the pertinent pharmacological descriptors and statistical analysis of their differences are shown in the Table. Pertinent regression parameters[a] (with confidence intervals [CI]), and statistical analysis of the dose-response curves illustrated in FIG. 4.

| anti-biotic | L. monocytogenes EGD+ | | | | |
|---|---|---|---|---|---|
| | $E^{max}$♦ (CI) | | $EC_{50}$◊ (CI) | $C_S$◊◊ | $R^2$ |
| CEM-101 | −0.66 (−1.28 to −0.037) a | mg/L | 0.020 (0.005 to 0.073) a | 0.11 | 0.934 |
| | | x MIC | 5.00 (1.36 to 18.5) a | 0.88 | |
| AZI | −0.81 (−2.11 to 0.48) a | mg/L | 2.66 (0.91 to 7.73) b | 11.6 | 0.953 |
| | | x MIC | 2.66 (0.81 to 3.1) a | 11.6 | |

| anti-biotic | L. pneumophila ATCC 33153++ | | | | |
|---|---|---|---|---|---|
| | $E_{max}$♦ (CI) | | $EC_{50}$◊ (CI) | $C_S$◊◊ | $R^2$ |
| CEM-101 | −1.03 (−1.34 to −0.72) a | mg/L | 0.052 (0.012 to 0.23) a | 0.018 | 0.920 |
| | | x MIC | 13.1 (3.02 to 57.0) a | 4.56 | |
| AZI | −0.83 (−2.00 to 0.34) a | mg/L | 2.86 (0.17 to 48.6) b | 2.90 | 0.903 |
| | | x MIC | 179.0 (10.5 to 3038) b | 181 | |

$^a$ using all data points shown in FIG. 4 (data from samples without antibiotics were not used because of evidence of extracellular growth when the extracellular concentration of an antibiotic is lower than 0.01 x MIC (5).
$^+$ original (post-phagocytosis) inoculum [time = 0h; CFU/mg protein]): L. monocytogenes, 1.67 ± 0.22 × 10$^6$ (n = 3); L. pneumophila, 0.94 ± 0.60 × 10$^6$.
♦ CFU decrease (in logo units) at time = 24 h (L. monocytogenes) or 48 h (L. pneumophila) from the corresponding original inoculum, as extrapolated for antibiotic concentration ∞; samples yielding less than 5 counts were considered below detection level.
◊ concentration (in mg/L or in x MIC) causing a reduction of the inoculum half-way between initial ($E_0$) and maximal ($E_{max}$) values, as obtained from the Hill equation (using a slope factor of 1).
◊◊ concentration (in mg/L or in x MIC) resulting in no apparent bacterial growth (number of CFU identical to the original inoculum), as determined by graphical intrapolation.
Statistical analyses: analysis of the differences between the two antibiotics (per column for the corresponding rows; unpaired, two-tailed t-test): figures with different lower case letters are significantly different from each other (p < 0.05).

EXAMPLE. Dose-response studies in infected THP-1 macrophages Against intraphagocytic S. aureus ATCC 25923, CEM-101 is more potent than AZI, CLR and TEL (lower Cs), In addition, CEM-101 is able to reduce the intracellular inoculum ($E_{max}$~1 log), which is not observed with any of AZI, CLR and TEL.

| CEM-101 uptake within cells (ii): role of the cell type | | | | |
|---|---|---|---|---|
| Cells | THP-1 (human macrophages) | J774 (murine macrophages) | MDCK (canine epith. cells) | MDCK sur-expressing the MDR1 efflux transporters |
| Cc/Ce at 5 h | ~50-150 | ~60 | ~45 | ~30 |

Figure 7:
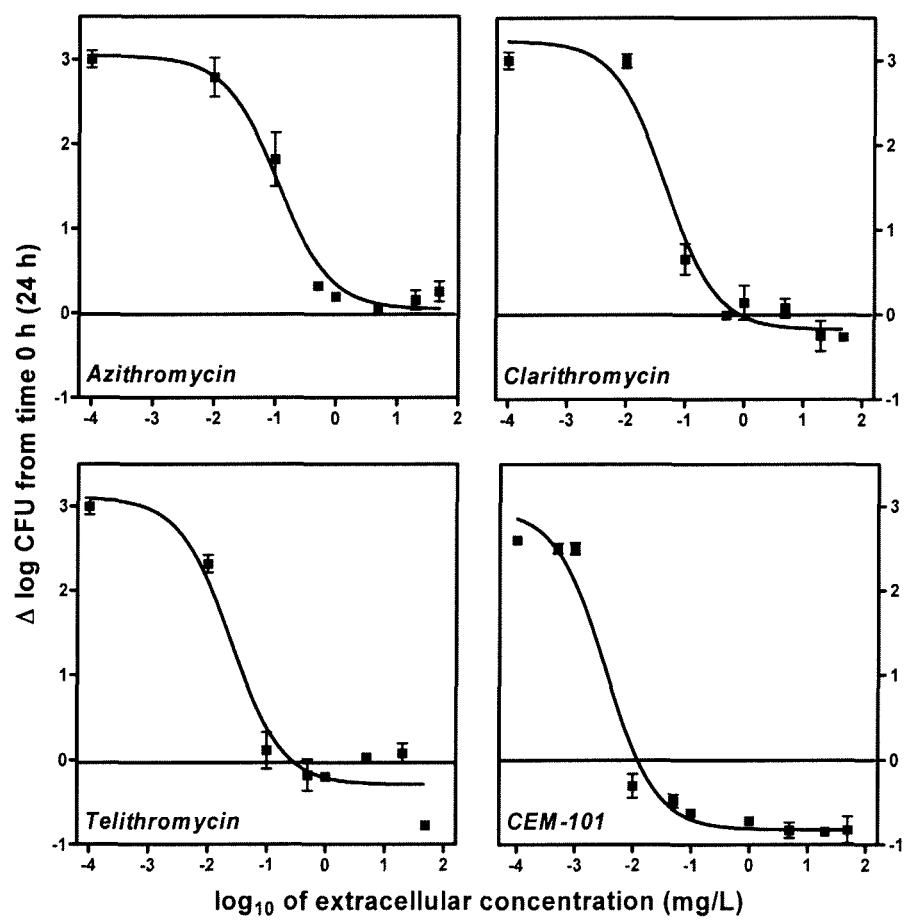
FIG. 7. Intracellular Activity of CEM-101 compared to AZI, CLR, and TEL, expressed as a dose response curve of Δ log CFU from time 0 to 24 hours versus log dose.

EXAMPLE. Example Dose-response studies of CEM-101 vs. comparators (AZI, CLR and TEL) against intracellular S. aureus ATCC 25923 (THP-1 macrophages). See FIG. 7 and the Table.

| | CEM-101 | AZI | CLR | TEL |
|---|---|---|---|---|
| Emax | −0.80 ± 0.11 | 0.04 ± 0.11 | −0.18 ± 0.13 | −0.29 ± 0.16 |
| Cs (mg/L) | ~0.01 | >50 | ~0.86 | ~0.27 |

Figure 6:
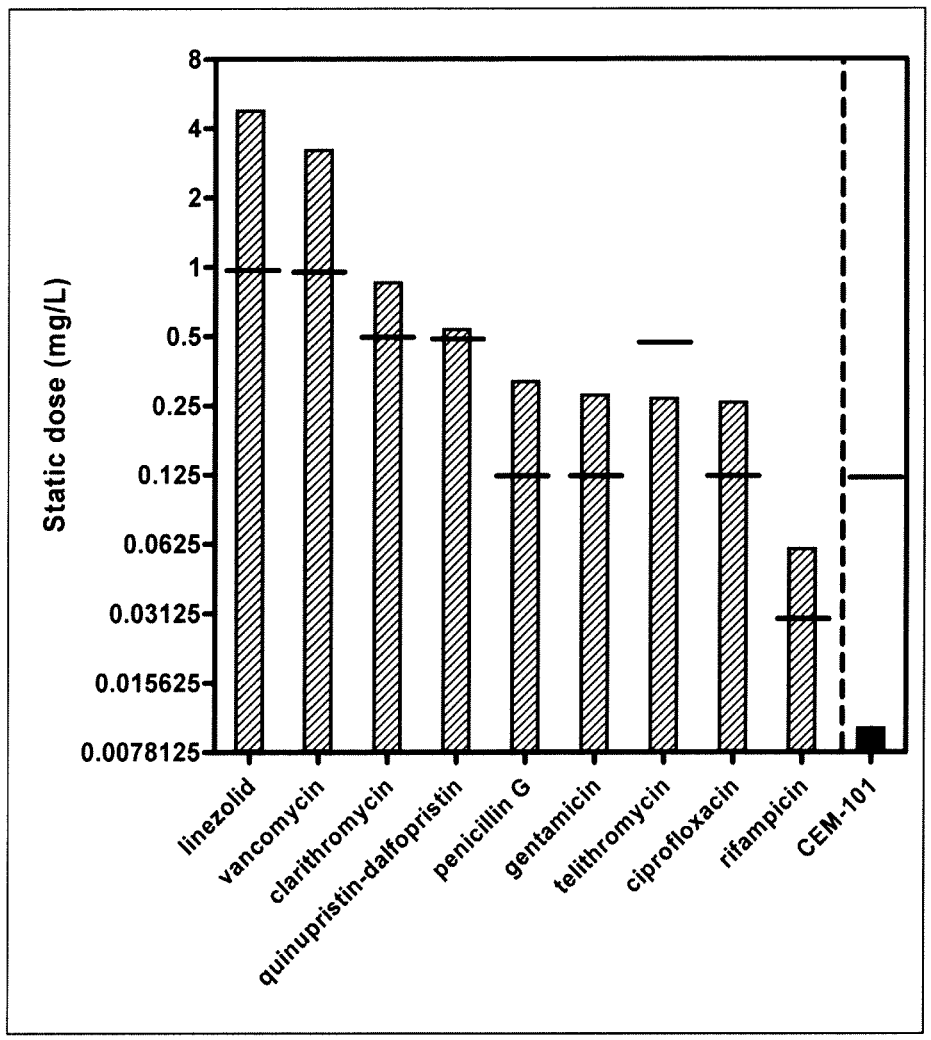
FIG. 6. Intracellular activity: comparative studies with other anti-staphylococcal agents. Comparative dose-static response of antibiotics against intracellular *Staphylococcus aureus* (strain ATCC 25923) in THP-1 macrophages. Bars represent the MICs (in mg/L) or the extracellular static dose.

EXAMPLE. Intracellular activity: comparative studies with other anti-staphylococcal agents. Comparative dose-static response of antibiotics against intracellular Staphylococcus aureus (strain ATCC 25923) in THP-1 macrophages were measured. See FIG. 6 bars represent the MICs (in mg/L) or the extracellular static dose.

METHOD. Mouse peritoneal macrophages were infected with viable M. leprae, the drugs are added and incubated at 33° C. for 3 days. After 3 days macrophages were lysed to release the intracellular M. leprae which were then assayed for viability by radiorespirometry and viability staining. CEM-101 shows efficacy against intracellular M. leprae viability.

The Thai-53 isolate of M. leprae, maintained by serial passages in athymic nu/nu mice footpads, was used for all experiments. For axenic testing freshly harvested viable M. leprae were incubated in medium along with different concentrations of the drugs (CEM-101, CLR and rifampin) for 7 days at 33° C. At the end of this incubation drug-treated M. leprae were subjected to radiorespirometry to assess viability based on oxidation of palmitate and staining with viability dyes to assess the extent of membrane damage. For intracellular testing peritoneal macrophages from Swiss mice were infected with freshly harvested viable M. leprae at an MOI of 20:1 for 12 hours. At the end of the infection extracellular bacteria were washed and drugs added at different concentrations and incubated for 3 days at 33° C. At the end of 3 days cells were lysed to obtain the intracellular M. leprae for radiorespirometry and viability staining.

CEM-101 at 0.15 μg/ml was able to significantly (P<0.001) reduce the viability of M. leprae in both axenic and intracellular cultures when compared to controls. Inhibition by CEM-101 was not statistically different from inhibition obtained with CLR under identical conditions and at the same concentration.

EXAMPLE. The high potency of CEM-101 against Streptococcus pneumoniae, β-haemolytic and viridans group streptococci, Staphylococcus spp. and enterococci has been documented in early screening studies performed using reference Clinical and Laboratory Standards Institute (CLSI) methods. Since mechanisms and occurrences of resistance are increasing rapidly that may compromise the MLSB-ketolide class, the bactericidal activity (MBC and killing curves) of CEM-101 with five selected classes of antimicrobial agents when testing wild type (WT) and phenotypically/genotypically defined resistant organism subsets was assessed. MBC determinations for CEM-101, TEL, and CLR used CLSI methods for 40 strains (6 species groups). KC used 8 strains (6 species groups). PAE was tested (5 strains) at 4× concentration for 1 or 2 hours exposure; TEL control.

MBC and killing curve studies: A total of 40 strains (10 S. pneumoniae, 10 S. aureus, and 5 each of β-haemolytic streptococci, viridans group streptococci, coagulase-negative staphylococci [CoNS] and enterococci) were MIC tested followed by MBC determinations using CLSI procedures (MIC and MBC range, 0.008-16 μg/ml). The lowest concentration of a tested agent that killed ≥99.9% of the initial inoculum was defined as the MBC endpoint (Tables 2 and 3). Time kill bactericidal activity was performed for CEM-101, TEL, CLR, and AZI on eight selected strains according to methods described by Moody & Knapp, NCCLS M21-A3 and M26-A. The compounds were tested at 2×, 4×, 8×MIC; and colony counts were performed at T0, T2, T4, T8 and T24.

CEM-101 exhibited low MBC/MIC ratios (≤4) for BSA, SA and coagulase-negative staphylococci; and 2-fold greater potency than TEL. SA, enterococci and some macrolide/CLN-resistant (R) strains had higher ratios. KC results showed more rapid and greater cidal activity (concentration dependant) for CEM-101 compared to TEL. CEM-101 exhibited cidal activity against several Gram-positive species at rates and an extent greater than TEL.

Distribution of isolates according to MBC/MIC ratio for CEM-101, TEL, CLR and AZI

| Organism/Antimicrobial agent (no. tested) | No. of strains with MBC/MIC value of: | | | | | |
|---|---|---|---|---|---|---|
| | 1 | 2 | 4 | 8 | 16 | ≥32 |
| *S. pneumoniae* (10) | | | | | | |
| CEM-101 | 3 | 5 | 0 | 0 | 0 | 2 |
| Telithromycin | 2 | 6[a] | 0 | 0 | 0 | 2 |
| Clarithromycin | 2 | 3 | 1 | 0 | 0 | —[b] |
| Azithromycin | 2 | 4 | 0 | 0 | 0 | —[b] |
| β-haemolytic *streptococci* (5) | | | | | | |
| CEM-101 | 0 | 1 | 2 | 0 | 0 | 2 |
| Telithromycin | 0 | 1 | 1 | 1 | 0 | 2 |
| Clarithromycin | 0 | 0 | 1 | 1 | 0 | 2[b] |
| Azithromycin | 0 | 0 | 0 | 0 | 2 | 2[b] |
| Viridans group *streptococci* (5) | | | | | | |
| CEM-101 | 3 | 0 | 1 | 0 | 0 | 1 |
| Telithromycin | 2 | 1 | 1 | 0 | 0 | 1 |
| Clarithromycin | 0 | 0 | 1 | 0 | 0 | 3[b] |
| Azithromycin | 0 | 0 | 0 | 0 | 1 | 3[b] |
| *S. aureus* (10) | | | | | | |
| CEM-101 | 1 | 0 | 0 | 0 | 1 | 8 |
| Telithromycin | 0 | 0 | 0 | 0 | 0 | 10 |
| Clarithromycin | 0 | 0 | 0 | 0 | 0 | 6[b] |
| Azithromycin | 0 | 0 | 0 | 0 | 0 | 6[b] |
| Coagulase-neg. *staphylococci* (5) | | | | | | |
| CEM-101 | 1 | 1 | 0 | 3 | 0 | 0 |
| Telithromycin | 0 | 0 | 0 | 0 | 2 | 3 |
| Clarithromycin | 0 | 0 | 0 | 0 | 0 | 4[b] |
| Azithromycin | 0 | 0 | 0 | 0 | 0 | 4[b] |
| *Enterococcus* spp. (5) | | | | | | |
| CEM-101 | 0 | 0 | 0 | 0 | 0 | 5 |
| Telithromycin | 0 | 0 | 0 | 0 | 0 | 5 |
| Clarithromycin | 0 | 0 | 0 | 0 | 0 | 2[b] |
| Azithromycin | 0 | 0 | 0 | 0 | 0 | 2[b] |

[a]Includes six isolates with a MIC of ≤0.008 µg/ml and a MBC of 0.015 µg/ml (off scale comparisons).
[b]MBC was not evaluated on isolates with resistant level MIC results.

CEM-101 showed rapid bactericidal activity (reduction of ≥3 log 10 CFU/ml) against macrolide-susceptible strains of *S. aureus, S. epidermidis, S. pneumoniae, S. pyogenes* (only at 8×MIC) and viridans group streptococci, as well as a macrolide-resistant *S. pyogenes*. CEM-101 produced a greater reduction of CFU/ml and more rapid killing when compared to either TEL or the macrolides CLR and AZI.

Summary of time kill curve results.

| Organism | Antimicrobial agent | Antimicrobial activity |
|---|---|---|
| *S. aureus* (ATCC 29213) | CEM-101 | Cidal at 2X, 4X, 8X |
| | Telithromycin | Cidal at 8X only |
| | Clarithromycin | Cidal at 8X only |
| | Azithromycin | Cidal at 8X only |
| *S. epidermidis* (095-2777A) | CEM-101 | Cidal at 2X, 4X, 8X |
| | Telithromycin | Static |
| | Clarithromycin | Static |
| | Azithromycin | Static |
| *E. faecalis* (ATCC 29212) | CEM-101 | Static |
| | Telithromycin | Static |
| | Clarithromycin | Static |
| | Azithromycin | Static |
| *S. pneumoniae* (ATCC 49619) | CEM-101 | Cidal at 2X, 4X, 8X |
| | Telithromycin | Cidal at 2X, 4X, 8X |
| | Clarithromycin | Cidal at 2X, 4X, 8X (slow killing) |
| | Azithromycin | Cidal at 2X, 4X, 8X (slow killing) |
| *S. pneumoniae* (075-241B) | CEM-101 | Static |
| | Telithromycin | Static |
| *S. pyogenes* (117-1612A) | CEM-101 | Cidal at 8X only |
| | Telithromycin | Cidal at 8X only (slow killing) |
| | Clarithromycin | Cidal at 8X only (slow killing) |
| | Azithromycin | Cidal at 8X only (slow killing) |
| *S. pyogenes* (088-11708A) | CEM-101 | Cidal at 2X, 4X, 8X |
| | Telithromycin | Cidal at 2X, 4X, 8X (slow killing) |
| *S. mitis* (112-1885A) | CEM-101 | Cidal at 2X, 4X, 8X |
| | Telithromycin | Cidal at 2X, 4X, 8X |
| | Clarithromycin | Cidal at 8X only (slow killing) |
| | Azithromycin | Cidal at 4X and 8X (slow killing) |

CEM-101 exhibited bactericidal activity when tested against macrolide-susceptible streptococci, CoNS and macrolide-resistant CLN-susceptible *S. pneumoniae*. CEM-101 MBC/MIC ratios can be high for *S. aureus*, but some strains showed MBC results remaining within the susceptible range of concentrations.

EXAMPLE. Activity on *Chlamydia*. CEM-101, TEL, AZI, CLR, and doxycycline were provided as powders and solubilized according to the instructions of the manufacturers. Drug suspensions were made fresh each time the assay was run.

*C. pneumoniae*: Isolates of *C. pneumoniae* tested included a reference strain (TW 183), 9 isolates from children and adults with pneumonia from the United States (AR39, T2023, T2043, W6805, CWL 029, CM-1), an isolate from a child with pneumonia from Japan (J-21), and 2 strains from bronchoalveolar lavage specimens from patients with human immunodeficiency virus infection and pneumonia from the United States (BAL15 and BAL16).

*C. trachomatis*: 10 isolates of *C. trachomatis*, including standard isolates from the ATCC (E-BOUR, F-IC-CAL3, C-HAR32, J-UW-36, L2434, D-UW-57kx, B-HAR-36) and recent clinical isolates (N18(cervical), N19(cervical), 7015 (infant eye))

In vitro susceptibility testing: Susceptibility testing of *C. pneumoniae* and *C. trachomatis* was performed in cell culture using HEp-2 cells grown in 96-well microtiter plates. Each well was inoculated with 0.1 ml of the test strain diluted to yield $10^3$ to $10^4$ IFU/per ml, centrifuged at 1,700×g for 1 hr. and incubated at 35° C. for 1 hr. Wells were aspirated and overlaid with 0.2 mL of medium containing 1 µg of cycloheximide per mL and serial two-fold dilutions of the test drug.

Duplicate plates were inoculated. After incubation at 35° C. for 48-72 hrs, cultures were fixed and stained for inclusions with fluorescein-conjugated antibody to the lipopolysaccharide genus antigen (Pathfinder, Kallestad Diagnostics, Chaska, Minn.). The minimal inhibitory concentration (MIC) is the lowest antibiotic concentration at which no inclusions were seen. The minimal bactericidal concentration (MBC) was determined by aspirating the antibiotic containing medium, washing wells twice with phosphate buffered saline and adding antibiotic-free medium. Cultures were frozen at −70° C., thawed, passed onto new cells, incubated for 72 hrs then fixed and stained as above. The MBC is the lowest antibiotic concentration that results in no inclusions after passage. All tests were run in triplicate.

| Activities of CEM-101 and other antibiotics against 10 isolates of C. pneumoniae | | | | | |
|---|---|---|---|---|---|
| | MIC (µg/ml) | | | MBC (µg/ml) | |
| Drug | Range | 50% | 90% | Range | 90% |
| CEM 101 | 0.25-1.0 | 0.25 | 0.25 | 0.25-1.0 | 0.25 |
| Telithromycin | 0.015-0.25 | 0.06 | 0.06 | 0.015-0.25 | 0.06 |
| Azithromycin | 0.015-0.125 | 0.125 | 0.125 | 0.015-0.125 | 0.125 |
| Clarithromycin | 0.015-0.125 | 0.06 | 0.06 | 0.015-0.125 | 0.06 |
| Doxycycline | 0.015-0.06 | 0.06 | 0.06 | 0.015-0.06 | 0.06 |

| Activities of CEM-101 and other antibiotics against 10 isolates of C. trachomatis | | | | | |
|---|---|---|---|---|---|
| | MIC (µg/ml) | | | MBC (µg/ml) | |
| Drug | Range | 50% | 90% | Range | 90% |
| CEM 101 | 0.125-0.5 | 0.25 | 0.25 | 0.125-0.5 | 0.25 |
| Telithromycin | 0.015-0.25 | 0.06 | 0.06 | 0.015-0.25 | 0.06 |
| Azithromycin | 0.015-0.125 | 0.125 | 0.125 | 0.015-0.125 | 0.125 |
| Clarithromycin | 0.015-0.125 | 0.06 | 0.06 | 0.015-0.125 | 0.06 |
| Doxycycline | 0.015-0.06 | 0.06 | 0.06 | 0.015-0.06 | 0.06 |

The results of this study demonstrated that CEM-101 has in vitro activity against C. trachomatis and C. pneumoniae comparable to other macrolides and ketolides.

EXAMPLE. Tissue distribution. CEM-101 was well absorbed and distributed to the tissue. In the rat at 250 mg/kg/d, mean lung and liver concentrations of CEM-101 were 17 and 15-fold higher than in plasma. Lung and liver concentrations were 503 and 711-fold higher than plasma concentrations at the 200 mg/kg/d dose in monkeys. Concentrations of CEM-101 in the heart were significantly lower than levels found in lung or liver with levels 5 and 54-fold higher than plasma concentrations in rat and monkey, respectively.

What is claimed is:

1. A method for treating a gastrointestinal disease caused by a bacteria in a host animal, the method comprising the step of administering to the host animal an effective amount of a compound of the formula

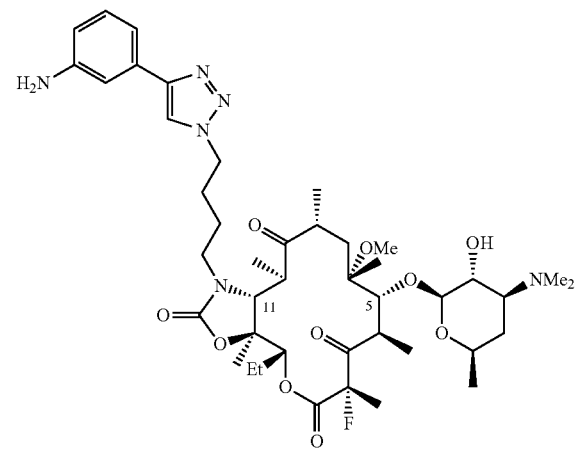 [SMILES: CC[C@H]1OC(=O)[C@@](C)(F)C(=O)[C@H](C)[C@@H](O[C@@H]2O[C@H](C)C[C@H](N(C)C)[C@H]2O)[C@@](C)(OC)C[C@@H](C)C(=O)[C@H](C)[C@H]2N(CCCCn3cc(-c4cccc(N)c4)nn3)C(=O)O[C@]12C]

or pharmaceutically acceptable salt thereof;
or an antibacterial composition thereof further comprising one or more pharmaceutically acceptable carriers, excipients, or diluents therefor, or a combination thereof.

2. A method for treating a gastrointestinal disease caused by a bacteria in a host animal, the method comprising the step of administering an effective amount of the compound recited in claim 1, or an antibacterial composition thereof further comprising one or more pharmaceutically acceptable carriers, excipients, or diluents therefor, or a combination thereof, wherein the effective amount is capable of killing the bacteria.

3. The method of claim 1 wherein the gastrointestinal disease is enteritis or gastroenteritis, or a combination thereof.

4. The method of claim 1 wherein the gastrointestinal disease is caused at least in part by an organism selected from the group consisting of Salmonella, Shigella, Staphylococcus, Campylobacter, Helicobacter, Clostridium, Escherichia coli, and Yersinia, and combinations thereof.

5. The method of claim 1 wherein the gastrointestinal disease is caused at least in part by H. pylori, C. jejuni, Salmonella, Shigella, or a combination thereof.

6. The method of claim 1 wherein the compound recited in claim 1 is of the formula

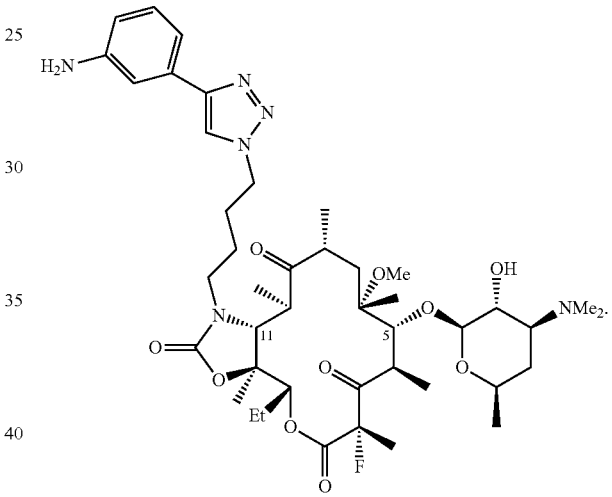

7. The method of claim 1 wherein the compound recited in claim 1 is of the formula

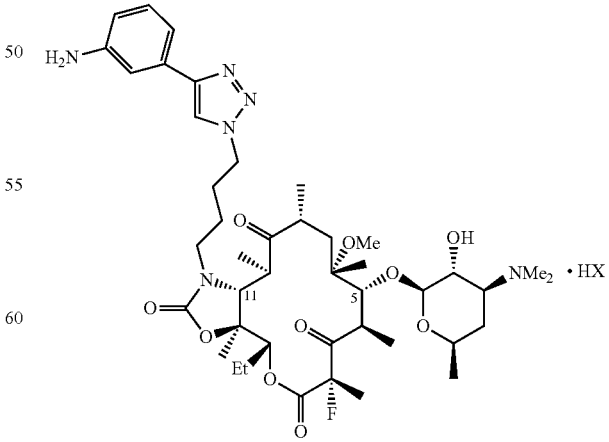

where HX is a pharmaceutically acceptable salt forming acid.

8. The method of claim 7 wherein HX is selected from the group consisting of hydrochloric acid, tartaric acid, and combinations thereof.

* * * * *